US011621077B2

(12) United States Patent
Neumann

(10) Patent No.: US 11,621,077 B2
(45) Date of Patent: Apr. 4, 2023

(54) METHODS AND SYSTEMS FOR USING ARTIFICIAL INTELLIGENCE TO SELECT A COMPATIBLE ELEMENT

(71) Applicant: Kenneth Neumann, Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 16/589,082

(22) Filed: Sep. 30, 2019

(65) Prior Publication Data

US 2021/0098129 A1     Apr. 1, 2021

(51) Int. Cl.
| | |
|---|---|
| *G16H 50/20* | (2018.01) |
| *G16H 50/30* | (2018.01) |
| *G06F 17/15* | (2006.01) |
| *G06K 9/62* | (2022.01) |
| *G06N 20/00* | (2019.01) |
| *G16H 10/60* | (2018.01) |

(52) U.S. Cl.
CPC ............. *G16H 50/20* (2018.01); *G06F 17/15* (2013.01); *G06K 9/6259* (2013.01); *G06N 20/00* (2019.01); *G16H 10/60* (2018.01); *G16H 50/30* (2018.01)

(58) Field of Classification Search
CPC ........ G16H 50/20; G16H 10/60; G16H 50/30; G16H 20/30; G16H 20/60; G06N 20/00; G06N 7/005; G06F 17/15; G06K 9/6259; G06K 9/6253; Y02A 90/10

USPC ........................................................ 705/2–3
See application file for complete search history.

(56) References Cited

U.S. PATENT DOCUMENTS

| | | | |
|---|---|---|---|
| 6,317,722 B1 | 11/2001 | Jacobi et al. | |
| 7,542,924 B2 | 6/2009 | Chow et al. | |
| 9,607,100 B1 | 3/2017 | Ware et al. | |
| 9,691,096 B1 | 6/2017 | Dai | |
| 9,720,974 B1* | 8/2017 | Sarmento | G06F 16/24573 |
| 9,978,070 B1 | 5/2018 | Peterson et al. | |
| 2013/0022275 A1* | 1/2013 | Inoue | G06F 16/583 |
| | | | 382/195 |
| 2014/0199709 A1* | 7/2014 | Gong | G01N 33/74 |
| | | | 435/7.4 |
| 2017/0138962 A1* | 5/2017 | Southern | G01N 33/6893 |
| 2017/0323057 A1* | 11/2017 | Karvela | G06K 7/10891 |
| 2018/0232689 A1* | 8/2018 | Minvielle | G06T 7/11 |
| 2019/0267128 A1* | 8/2019 | Decombel | G16H 20/60 |
| 2019/0295440 A1* | 9/2019 | Hadad | G06F 40/137 |

(Continued)

*Primary Examiner* — Joshua B Blanchette
*Assistant Examiner* — Tran N Nguyen
(74) *Attorney, Agent, or Firm* — Caldwell Intellectual Property Law

(57) ABSTRACT

A system for using artificial intelligence to select a compatible element. The system includes at least a server wherein the at least a server is configured to receive training data. The at least a server is configured to receive at least a biological extraction from a user. The at least a server is configured to receive at least a datum of user activity data. The at least a server is configured to select at least a compatible element as a function of the training data, the at least a biological extraction, and the at least a user activity data. The at least a server is configured to transmit the at least a compatible element to a user client device.

12 Claims, 14 Drawing Sheets

(56) References Cited

U.S. PATENT DOCUMENTS

2019/0304000 A1\* 10/2019 Simpson .............. G01N 33/492
2020/0321111 A1\* 10/2020 Neumann .............. G16H 50/00

\* cited by examiner

METHODS AND SYSTEMS FOR USING ARTIFICIAL INTELLIGENCE TO SELECT A COMPATIBLE ELEMENT

FIELD OF THE INVENTION

The present invention generally relates to the field of artificial intelligence. In particular, the present invention is directed to methods and systems for using artificial intelligence to select a compatible element.

BACKGROUND

Accurate selection of compatible elements can be challenging due to the multitude of factors to be considered. Analyzing large quantities of data can be challenging due to the complexity of what currently exists. Incorrect selection of compatible elements can lead to inaccuracies and ultimately frustrate users.

SUMMARY OF THE DISCLOSURE

In an aspect, a system for using artificial intelligence to select a compatible element. The system includes at least a system. At least a server is designed and configured to receive training data, wherein receiving training data further comprises receiving a first training set including a plurality of first data entries, each first data entry of the plurality of first data entries including at least an element of physiological state data and at least a correlated compatible label. At least a server is configured to receive at least a biological extraction from a user. At least a server is configured to receive at least a datum of user activity data. At least a server is configured to select at least a compatible element as a function of the training data, biological extraction, and user activity data. At least a server is configured to transmit the at least a compatible element to a user client device.

In an aspect, a method of using artificial intelligence to select a compatible element. The method includes receiving training data, wherein receiving training data further comprises receiving a first training set including a plurality of first data entries, each first data entry of the plurality of first data entries including at least an element of physiological state data and at least a correlated compatible label. The method includes receiving at least a biological extraction from a user. The method includes receiving at least a datum of user activity data. The method includes selecting at least a compatible element as a function of the training data, biological extraction, and user activity data. The method includes transmitting the at least a compatible element to a user client device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for using artificial intelligence to select a compatible element. In an embodiment, at least a server receives user data. User data may include for example a biological extraction and a datum of user activity data. At least a server uses user data in combination with training data to select at least a compatible element. At least a compatible element may be transmitted to a user client device.

Figure 1:
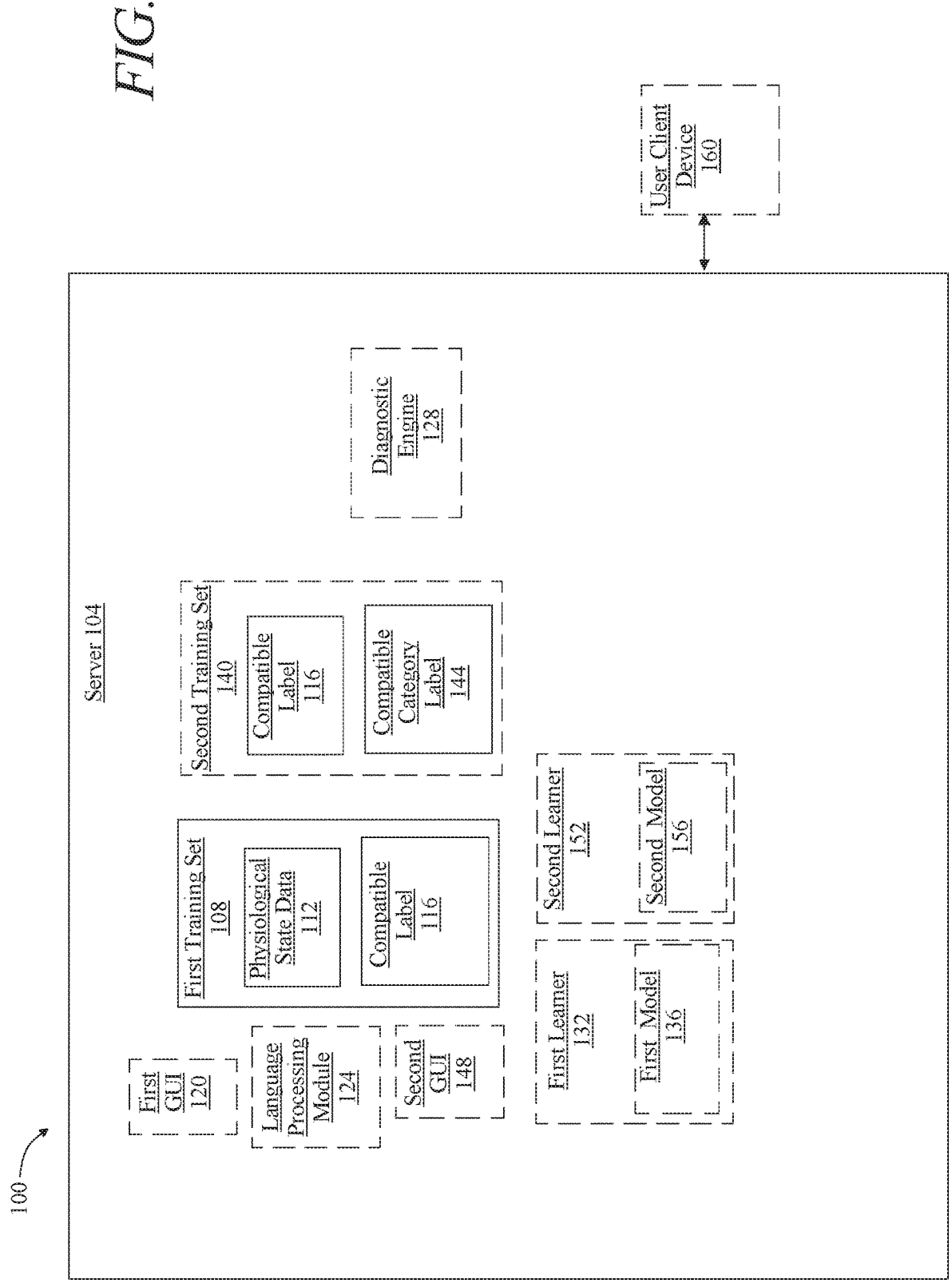
FIG. 1 is a block diagram illustrating an exemplary embodiment of a system for using artificial intelligence to select a compatible element.

Turning now to FIG. 1, an artificial intelligence system 100 to select a compatible element is illustrated. System 100 includes at least a server 104. At least a server 104 may include any computing device as described herein, including without limitation a microcontroller, microprocessor, digital signal processor (DSP) and/or system on a chip (SoC) as described herein. At least a server 104 may be housed with, may be incorporated in, or may incorporate one or more sensors of at least a sensor. Computing device may include, be included in, and/or communicate with a mobile device such as a mobile telephone or smartphone. At least a server 104 may include a single computing device operating independently, or may include two or more computing device operating in concert, in parallel, sequentially or the like; two or more computing devices may be included together in a single computing device or in two or more computing devices. At least a server 104 with one or more additional devices as described below in further detail via a network interface device. Network interface device may be utilized for connecting a at least a server 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. At least a server 104 may include but is not limited to, for example, a at least a server 104 or cluster of computing devices in a first location and a second computing device or cluster of computing devices in a second location. At least a server 104 may include one or more computing devices dedicated to data storage, security, distribution of traffic for load balancing, and the like. At least a server 104 may distribute one or more computing tasks as described below across a plurality of computing devices of computing device, which may operate in parallel, in series, redundantly, or in any other manner used for distribution of tasks or memory between computing devices. At least a server 104 may be implemented using a "shared nothing" architecture in which data is cached at the worker, in an embodiment, this may enable scalability of system 100 and/or computing device.

With continued reference to FIG. 1, at least a server 104 is configured to receive training data. Training data, as used herein, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name and/or a description of a medical condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

With continued reference to FIG. 1, at least a server 104 is configured to receive a first training set 108 including a plurality of first data entries, each first data entry of the first training set 108 including at least an element of physiological state data 112 and at least a correlated compatible label 116. At least an element of physiological state data 112 as used herein, includes any data indicative of a person's physiological state. A compatible label 116 as used herein, includes any identifier of any compatible element that is compatible with a user. Compatible element, as used herein, includes one or more products, ingredients, merchandise, additive, component compound, mixture, constituent, element, article, and/or information content that is compatible with a user as described in more detail below. At least an element of physiological state data 112 may include any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. Physiological state data 112 may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data 112 may include, without limitation, immune function data such as Interleukine-6 (IL-6), TNF-alpha, systemic inflammatory cytokines, and the like.

Continuing to refer to FIG. 1, physiological state data 112 may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data 112 may include measures of glucose metabolism such as fasting glucose levels and/or hemoglobin A1-C(HbA1c) levels. Physiological state data 112 may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data 112 may include measures of estimated glomerular filtration rate (eGFR). Physiological state data 112 may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data 112 may include antinuclear antibody levels. Physiological state data 112 may include aluminum levels. Physiological state data 112 may include arsenic levels. Physiological state data 112 may include levels of fibrinogen, plasma cystatin C, and/or brain natriuretic peptide.

Continuing to refer to FIG. 1, physiological state data 112 may include measures of lung function such as forced expiratory volume, one second (FEV-1) which measures how much air can be exhaled in one second following a deep inhalation, forced vital capacity (FVC), which measures the volume of air that may be contained in the lungs. Physiological state data 112 may include a measurement blood pressure, including without limitation systolic and diastolic blood pressure. Physiological state data 112 may include a measure of waist circumference. Physiological state data 112 may include body mass index (BMI). Physiological state data 112 may include one or more measures of bone mass and/or density such as dual-energy x-ray absorptiometry. Physiological state data 112 may include one or more measures of muscle mass. Physiological state data 112 may include one or more measures of physical capability such as without limitation measures of grip strength, evaluations of standing balance, evaluations of gait speed, pegboard tests, timed up and go tests, and/or chair rising tests.

Still viewing FIG. 1, physiological state data 112 may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data 112 may include one or more measures of psychological function or state, such as without limitation clinical interviews, assessments of intellectual functioning and/or intelligence quotient (IQ) tests, personality assessments, and/or behavioral assessments. Physiological state data 112 may include one or more psychological self-assessments, which may include any self-administered and/or automatedly computer-administered assessments, whether administered within system 100 and/or via a third-party service or platform.

Continuing to refer to FIG. 1, physiological state data 112 may include psychological data. Psychological data may include any data generated using psychological, neuropsychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chatrooms or the like, any textual, image, video, and/or data produced by the subject, any textual image, video and/or other data depicting and/or describing the subject, or the like. Any psychological data and/or data used to generate psychological data may be analyzed using machine-learning and/or language processing module 124 144 as described in this disclosure.

With continued reference to FIG. 1, physiological state data 112 may include one or more evaluations of sensory ability, including measures of audition, vision, olfaction, gustation, vestibular function and pain. Physiological state data 112 may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data 112 may include proteomic data, which as used herein, is data describing all proteins produced and/or modified by an organism, colony of organisms, or system of organisms, and/or a subset thereof. Physiological state data 112 may include data concerning a microbiome of a person, which as used herein, includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data 112 of a person, and/or on compatible label 116 and/or ameliorative processes as described in further detail below. Physiological state data 112 may include any physiological state data 112, as described above, describing any multicellular organism living in or on a person including any parasitic and/or symbiotic organisms living in or on the persons; non-limiting examples may include mites, nematodes, flatworms, or the like.

With continuing reference to FIG. 1, physiological state data 112 may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Examples of physiological state data 112 described in this disclosure are presented for illustrative purposes only and are not meant to be exhaustive. Persons skilled in the art, upon reviewing the entirety of this disclosure, will be aware of various additional examples of physiological state data 112 that may be used consistently with descriptions of systems and methods as provided in this disclosure.

With continued reference to FIG. 1, each element of first training set 108 includes at least a correlated compatibility label. A correlated compatibility label, as described herein, is an element of data identifying and/or describing any product, ingredient, element, merchandise, additive, component, compound, mixture, constituent, element, article, and/or information content that is compatible with a user as a function of a user's biological extraction. A product may include for example, goods such as but not limited to beauty products, books, electronics, art, food and grocery, health and personal goods, home and garden, appliances, music, office goods, outdoor goods, sporting goods, tools, toys, home improvement, video, digital versatile disc (DVD), blue-ray, jewelry, musical instruments, computers, cell phones, movies, and the like.

With continued reference to FIG. 1, a correlated compatibility label may be associated with one or more elements of physiological state data 112. For example, a correlated compatibility label for a product such as shampoo containing parabens may be associated with one or more biological extractions including Apolipoprotein E Gene 2 (APOE2) and Apolipoprotein E Gene 3 (APOE3) and not Apolipoprotein E Gene 4 (APOE4). In yet another non-limiting example, a correlated compatibility label for a product containing dextromethorphan may be associated with one or more elements of physiological data including gene profiles such as extensive metabolizers and ultra-rapid metabolizers and not poor metabolizer. In yet another non-limiting example, a correlated compatibility label for literature describing the benefits of melatonin in breast cancer treatment may be associated with one or more elements of physiological data including positive test results indicating a current breast cancer diagnosis, as well as biological extractions indicating the presence of the breast cancer gene 1 (BRCA1), breast cancer gene 2 (BRCA2), and cyclin-dependent kinase inhibitor 1B gene (CDKN1B). In yet another non-limiting example, a correlated advisory label for a product containing classical music may be associated with one or more elements of physiological data including a positive pregnancy test, a positive evaluation for anxiety, and a positive evaluation for depression. In yet another non-limiting example, a correlated advisory label for organic makeup may be associated with one or more elements of physiological data including an elevated thyroid stimulating hormone (TSH), an elevated c-reactive protein (CRP), and an elevated erythrocyte sedimentation rate (ESR).

With continued reference to FIG. 1, correlated compatibility label may be stored in any suitable data and/or data type. For instance, and without limitation, correlated compatibility label may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as at least a compatibility label may take; persons skilled in the art, upon reviewing the entirety of this disclosure, will be aware of various forms which may be suitable for use as at least an advisory label consistently with this disclosure.

With continued reference to FIG. 1, correlated compatibility label may be stored as image data, such as for example an image of a particular product such as a photograph of a particular sunscreen product or an image of a particular book. Image data may be stored in various forms including for example, joint photographic experts group (JPEG), exchangeable image file format (Exif), tagged image file format (TIFF), graphics interchange format (GIF), portable network graphics (PNG), netpbm format, portable bitmap (PBM), portable any map (PNM), high efficiency image file format (HEIF), still picture interchange file format (SPIFF), better portable graphics (BPG), drawn filed, enhanced compression wavelet (ECW), flexible image transport system (FITS), free lossless image format (FLIF), graphics environment manage (GEM), portable arbitrary map (PAM), personal computer exchange (PCX), progressive graphics file (PGF), gerber formats, 2 dimensional vector formats, 3 dimensional vector formats, compound formats including both pixel and vector data such as encapsulated postscript (EPS), portable document format (PDF), and stereo formats.

With continued reference to FIG. 1, in each first data element of first training set 108 at least an element of physiological state data 112 is correlated with a compatible label 116 where the element of physiological data is located in the same data element and/or portion of data element as the compatible label 116; for example, and without limitation, an element of physiological data is correlated with a correlated element where both element of physiological data and correlated element are contained within the same first data element of the first training set. As a further example, an element of physiological data is correlated with a correlated element where both share a category label as described in further detail below, where each is within a certain distance of the other within an ordered collection of data in data element, or the like. Still further, an element of physiological data may be correlated with a correlated element where the element of physiological data and the correlated element share an origin, such as being data that was collected with regard to a single person or the like. In an embodiment, a first datum may be more closely correlated with a second datum in the same data element than with a third datum contained in the same data element; for instance, the first element and the second element may be closer to each other in an ordered set of data than either is to the third element, the first element and second element may be contained in the same subdivision and/or section of data while the third element is in a different subdivision and/or section of data, or the like. Persons skilled in the art, upon reviewing the entirety of this disclosure, will be aware of various forms and/or degrees of correlation between physiological data and compatible label 116 that may exist in first training set 108 and/or first data element consistently with this disclosure.

With continued reference to FIG. 1, at least a server 104 may be designed and configured to associate at least an element of physiological state data 112 with at least a category from a list of significant categories of physiological state data 112. Significant categories of physiological state data 112 may include labels and/or descriptors describing types of physiological state data 112 that are identified as being of high relevance in identifying compatible label 116. As a non-limiting example, one or more categories may identify significant categories of physiological state data 112 based on degree of diagnostic relevance to one or more impactful conditions and/or within one or more medical or public health fields. For instance, and without limitation, a particular set of biomarkers, test results, and/or biochemical information may be recognized in a given medical field as useful for identifying various disease conditions or associated ingredients and products that may be compatible with a particular disease or condition as well as associated ingredients and products that may not be compatible with a particular disease or condition. As a non-limiting example, and without limitation, physiological data describing disorders associated with heavy metal accumulation including for example heart disease, Lyme disease, and Multiple Sclerosis may be useful in selecting compatible label 116 that include organic ingredients free of heavy metals such as lead, mercury, arsenic, cadmium, and chromium. As an additional example, physiological data associated with mental disorders such as anxiety, bipolar disorder, depression, and schizophrenia may be useful in selecting compatible label 116 that include music products with calming music such as classical music, smooth jazz, blues, and elevator music. In a further non-limiting example, physiological data describing disorders such as an allergic dermatitis to certain metals such as nickel or lead may be useful in selecting compatible label 116 that include jewelry that is free of such ingredients. Persons skilled in the art, upon reviewing the entirety of this disclosure, will be aware of various additional categories of physiological data that may be used consistently with this disclosure.

Still referring to FIG. 1, at least a server 104 may receive the list of significant categories according to any suitable process; for instance, and without limitation, at least a server 104 may receive the list of significant categories from at least an expert. In an embodiment, at least a server 104 may provide a graphical user interface, which may include without limitation a form or other graphical element having data entry fields, wherein one or more experts, including without limitation clinical and/or scientific experts, may enter information describing one or more categories of physiological data that the experts consider to be significant or useful for detection of conditions; fields in graphical user interface may provide options describing previously identified categories, which may include a comprehensive or near-comprehensive list of types of physiological data detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. First graphical user interface 120 or the like may include fields corresponding to compatible label 116, where experts may enter data describing compatible label 116 and/or categories of compatible label 116 the experts consider related to entered categories of physiological data; for instance, such fields may include drop-down lists or other pre-populated data entry fields listing currently recorded compatible label 116, and which may be comprehensive, permitting each expert to select a compatible label 116 and/or a plurality of compatible label 116 the expert believes to be predicted and/or associated with each category of physiological data selected by the expert. Fields for entry of compatible label 116 and/or categories of compatible label 116 may include free-form data entry fields such as text entry fields; as described above, examiners may enter data not presented in pre-populated data fields in the free-form data entry fields. Alternatively or additionally, fields for entry of compatible label 116 may enable an expert to select and/or enter information describing or linked to a category of compatible label 116 that the expert considers significant, where significance may indicate likely impact on longevity, mortality, quality of life, or the like as described in further detail below. First graphical user interface 120 may provide an expert with a field in which to indicate a reference to a document describing significant categories of physiological data, relationships of such categories to compatible label 116, and/or significant categories of compatible label 116. Any data described above may alternatively or additionally be received from experts similarly organized in paper form, which may be captured and entered into data in a similar way, or in a textual form such as a portable document file (PDF) with examiner entries, or the like.

With continued reference to FIG. 1, data information describing significant categories of physiological data, relationships of such categories to compatible label 116, and/or significant categories of compatible label 116 may alternatively or additionally be extracted from one or more documents using a language processing module 124. Language processing module 124 may include any hardware and/or software module. Language processing module 124 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module 124 may compare extracted words to categories of physiological data recorded by at least a server 104, one or more compatible label 116 recorded by at least a server 104, and/or one or more categories of compatible label 116 recorded by at least a server 104; such data for comparison may be entered on at least a server 104 as described above using expert data inputs or the like. In an embodiment, one or more categories may be enumerated, to find total count of mentions in such documents. Alternatively or additionally, language processing module 124 may operate to produce a language processing model. Language processing model may include a program automatically generated by at least a server 104 and/or language processing module 124 to produce associations between one or more words extracted from at least a document and detect associations, including without limitation mathematical associations, between such words, and/or associations of extracted words with categories of physiological data, relationships of such categories to compatible label 116, and/or categories of compatible label 116. Associations between language elements, where language elements include for purposes herein extracted words, categories of physiological data, relationships of such categories to compatible label 116, and/or categories of compatible label 116 may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to compatible label 116, and/or a given category of compatible label 116. As a further example, statistical correlations and/or mathematical associations may include probabilistic formulas or relationships indicating a positive and/or negative association between at least an extracted word and/or a given category of physiological data, a given relationship of such categories to compatible label 116, and/or a given category of compatible label 116; positive or negative indication may include an indication that a given document is or is not indicating a category of physiological data, relationship of such category to compatible label 116, and/or category of compatible label 116 is or is not significant. For instance, and without limitation, a negative indication may be determined from a phrase such as "phthalates were not found to increase the risk of testicular cancer," whereas a positive indication may be determined from a phrase such as "phthalates were found to increase the risk of breast cancer," as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory by at least a server 104, or the like.

Still referring to FIG. 1, language processing module 124 and/or at least a server 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein, are statistical models with inference algorithms that that may be applied to the models. In such models, a hidden state to be estimated may include an association between an extracted word category of physiological data, a given relationship of such categories to compatible label 116, and/or a given category of compatible label 116. There may be a finite number of category of physiological data, a given relationship of such categories to compatible label 116, and/or a given category of compatible label 116 to which an extracted word may pertain; an HMM inference algorithm, such as the forward-backward algorithm or the Viterbi algorithm, may be used to estimate the most likely discrete state given a word or sequence of words. Language processing module 124 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 124 may use a corpus of documents to generate associations between language elements in a language processing module 124 and at least a server 104 may then use such associations to analyze words extracted from one or more documents and determine that the one or more documents indicate significance of a category of physiological data, a given relationship of such categories to compatible label 116, and/or a given category of compatible label 116. In an embodiment, at least a server 104 may perform this analysis using a selected set of significant documents, such as documents identified by one or more experts as representing good science, good clinical analysis, or the like; experts may identify or enter such documents via graphical user interface, or may communicate identities of significant documents according to any other suitable method of electronic communication, or by providing such identity to other persons who may enter such identifications into at least a server 104. Documents may be entered into at least a server 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, at least a server 104 may automatically obtain the document using such an identifier, for instance by submitting a request to a database or compendium of documents such as JSTOR as provided by Ithaka Harbors, Inc. of New York.

Continuing to refer to FIG. 1, whether an entry indicating significance of a category of physiological data, a given relationship of such categories to compatible label 116, and/or a given category of compatible label 116 is entered via graphical user interface, alternative submission means, and/or extracted from a document or body of documents as described above, an entry or entries may be aggregated to indicate an overall degree of significance. For instance, each category of physiological data, relationship of such categories to compatible label 116, and/or category of compatible label 116 may be given an overall significance score; overall significance score may, for instance, be incremented each time an expert submission and/or paper indicates significance as described above. Persons skilled in the art, upon reviewing the entirety of this disclosure will be aware of other ways in which scores may be generated using a plurality of entries, including averaging, weighted averaging, normalization, and the like. Significance scores may be ranked; that is, all categories of physiological data, relationships of such categories to compatible label 116, and/or categories of compatible label 116 may be ranked according significance scores, for instance by ranking categories of physiological data, relationships of such categories to compatible label 116, and/or categories of compatible label 116 higher according to higher significance scores and lower according to lower significance scores. Categories of physiological data, relationships of such categories to compatible label 116, and/or categories of compatible label 116 may be eliminated from current use if they fail a threshold comparison, which may include a comparison of significance score to a threshold number, a requirement that significance score belong to a given portion of ranking such as a threshold percentile, quartile, or number of top-ranked scores. Significance scores may be used to filter outputs as described in further detail below; for instance, where a number of outputs are generated and automated selection of a smaller number of outputs is desired, outputs corresponding to higher significance scores may be identified as more probable and/or selected for presentation while other outputs corresponding to lower significance scores may be eliminated. Alternatively or additionally, significance scores may be calculated per sample type; for instance, entries by experts, documents, and/or descriptions of purposes of a given type of physiological test or sample collection as described above may indicate that for that type of physiological test or sample collection a first category of physiological data, relationship of such category to compatible label 116, and/or category of compatible label 116 is significant with regard to that test, while a second category of physiological data, relationship of such category to compatible label 116, and/or category of compatible label 116 is not significant; such indications may be used to perform a significance score for each category of physiological data, relationship of such category to compatible label 116, and/or category of compatible label 116 is or is not significant per type of physiological sample, which then may be subjected to ranking, comparison to thresholds and/or elimination as described above.

Still referring to FIG. 1, at least a server 104 may detect further significant categories of physiological data, relationships of such categories to compatible label 116, and/or categories of compatible label 116 using machine-learning processes, including without limitation unsupervised machine-learning processes as described in further detail below; such newly identified categories, as well as categories entered by experts in free-form fields as described above, may be added to pre-populated lists of categories, lists used to identify language elements for language learning module, and/or lists used to identify and/or score categories detected in documents, as described above.

Continuing to refer to FIG. 1, in an embodiment, at least a server 104 may be configured, for instance as part of receiving the first training set, to associate at least a correlated first compatible label 116 with at least a category from a list of significant categories of compatible label 116. Significant categories of compatible label 116 may be acquired, determined, and/or ranked as described above. As a non-limiting example, compatible label 116 may be organized according to relevance to and/or association with a list of significant conditions. A list of significant conditions may include, without limitation, conditions having generally acknowledged impact on longevity and/or quality of life; this may be determined, as a non-limiting example, by a product of relative frequency of a condition within the population with years of life and/or years of able-bodied existence lost, on average, as a result of the condition. A list of conditions may be modified for a given person to reflect a family history of the person; for instance, a person with a significant family history of a particular condition or set of conditions, or a genetic profile having a similarly significant association therewith, may have a higher probability of developing such conditions than a typical person from the general population, and as a result at least a server 104 may modify list of significant categories to reflect this difference.

With continued reference to FIG. 1, at least a server 104 is configured to receive at least a biological extraction from a user. At least a biological extraction, as used herein, includes may include any element and/or elements of data suitable for use as an element of physiological state data 112. At least a biological extraction may include a physically extracted sample, which as used herein includes a sample obtained by removing and analyzing tissue and/or fluid. Physically extracted sample may include without limitation a blood sample, a tissue sample, a buccal swab, a mucous sample, a stool sample, a hair sample, a fingernail sample, or the like. Physically extracted sample may include, as a non-limiting example, at least a blood sample. As a further non-limiting example, at least a biological extraction may include at least a genetic sample. At least a genetic sample may include a complete genome of a person or any portion thereof. At least a genetic sample may include a DNA sample and/or an RNA sample. At least a biological extraction may include an epigenetic sample, a proteomic sample, a tissue sample, a biopsy, and/or any other physically extracted sample. At least a biological extraction may include an endocrinal sample. As a further non-limiting example, the at least a biological extraction may include a signal from at least a sensor configured to detect physiological data of a user and recording the at least a biological extraction as a function of the signal. At least a sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. At least a sensor may include any electromagnetic sensor, including without limitation electroencephalographic sensors, magnetoencephalographic sensors, electrocardiographic sensors, electromyographic sensors, or the like. At least a sensor may include a temperature sensor. At least a sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. At least a sensor may detect any hematological parameter including blood oxygen level, pulse rate, heart rate, pulse rhythm, and/or blood pressure. At least a sensor may be a part of at least a server 104 or may be a separate device in communication with at least a server 104.

Still referring to FIG. 1, at least a biological extraction may include any data suitable for use as physiological state data 112 as described above, including without limitation any result of any medical test, physiological assessment, cognitive assessment, psychological assessment, or the like. System 100 may receive at least a biological extraction from one or more other devices after performance; system 100 may alternatively or additionally perform one or more assessments and/or tests to obtain at least a biological extraction, and/or one or more portions thereof, on system 100. For instance, at least biological extraction may include or more entries by a user in a form or similar graphical user interface object; one or more entries may include, without limitation, user responses to questions on a psychological, behavioral, personality, or cognitive test. For instance, at least a server 104 may present to user a set of assessment questions designed or intended to evaluate a current state of mind of the user, a current psychological state of the user, a personality trait of the user, or the like; at least a server 104 may provide user-entered responses to such questions directly as at least a biological extraction and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

Alternatively or additionally, and with continued reference to FIG. 1, at least a biological extraction may include assessment and/or self-assessment data, and/or automated or other assessment results, obtained from a third-party device; third-party device may include, without limitation, a server 104 or other device (not shown) that performs automated cognitive, psychological, behavioral, personality, or other assessments. Third-party device may include a device operated by an informed advisor such a functional health care professional including for example a functional medicine doctor.

Still referring to FIG. 1, at least a biological extraction may include data describing one or more test results, including results of mobility tests, stress tests, dexterity tests, endocrinal tests, genetic tests, and/or electromyographic tests, biopsies, radiological tests, genetic tests, and/or sensory tests. At least a server 104 may be configured to record at least a biological extraction from a user. Persons skilled in the art, upon reviewing the entirety of this disclosure, will be aware of various additional examples of at least a biological extraction consistent with this disclosure.

With continued reference to FIG. 1, at least a server 104 is configured to receive at least a datum of user activity data. A datum of user activity as used herein, includes any data describing a user's current and/or previous interaction with system 100. A datum of user activity may include data describing a user's previously selected and/or purchased products, currently selected and/or purchased products, ingredients, merchandise, additive, component, compound, mixture, constituent, and/or element. For example, a datum of user activity may include data describing a list of items user purchased last week. In yet another non-limiting example, a datum of user activity may include data describing a list of items a user browsed from two months back but did not purchase. In yet another non-limiting example, a datum of user activity may include data describing a particular product user intended to purchase such as by placing it in an electronic shopping cart but never followed through and purchased. A datum of user activity may include data describing a user's activity that is linked to several accounts a user may have. For example, a user may have a personal account associated with system 100 in addition to a business account associated with system 100. In such an instance, data describing user's previous interaction with user's business account may be provided, data describing user's previous interaction with user's personal account may be provided, and/or a combination of the both. In yet another non-limiting example, at least a datum of user activity data may include data describing a particular brand or categories of brands that user viewed and/or purchased products from. For example, a datum of user activity data may include data describing three products from a first brand user viewed and two products from a second brand user purchased. In an embodiment, datum of user activity data may include historical data such as browsing and/or purchasing history that occurred at any time in the past. In yet another example, a datum of user activity data may include current real time data describing current browsing and/or purchasing history that user is actively engaged upon at the present moment.

With continued reference to FIG. 1, at least a server 104 is configured to select at least a first compatible element as a function of the training data, biological extraction from a user, and user activity data. A compatible element, as used herein, includes one or more products, ingredients, merchandise, additive, component compound, mixture, constituent, element, article, and/or informational content that is compatible with a user. A compatible element may include a particular brand of product, a particular ingredient contained within a product, a particular category of products, a particular category of ingredients, a particular product line, a particular ingredient line. For example, a compatible element may include a shampoo that contains ingredients that won't cause user's seborrheic eczema to flare up. In yet another non-limiting example, a compatible element may include a list of music artists that won't worsen a user's intermittent explosive disorder. In yet another non-limiting example, a compatible element may include a list of makeup free of mold for a user with mold toxicity. In yet another non-limiting example, compatible element may contain a list of cleaning products free of gluten for a user with Celiac Disease. Compatibility includes one or more products, ingredients, merchandise, additive, component compound, mixture, constituent, element, article, and/or informational content that is capable of use and/or consumption by a user without an adverse effect. An adverse effect may include any negative effect on longevity, health condition, mortality, and/or quality of life of a user. For example, a user with dermatitis herpetiformis who uses hand soap containing gluten may experience an adverse response such as a blistering rash on body parts exposed to gluten containing hand soap. In yet another non-limiting example, a user with small intestinal bacterial overgrowth (SIBO) who consumes kombucha rich in microorganisms may experience an adverse response such as bloating, gas, and diarrhea. In yet another non-limiting example, a user with breast cancer susceptibility gene (BRCA 1 or BRCA 2) who uses personal care items containing phthalates may experience an adverse effect such as a greater risk of developing breast cancer. In an embodiment, a compatible element containing a plurality of products and/or ingredients may be ranked in order of compatibility. For example, a compatible element containing three shampoos that may be suitable for use by a user with a lactose allergy may be listed in order of compatibility from most compatible down to least compatible. In such an instance, products and/or ingredients may be ranked such as for example most compatible if a product was manufactured in a certified lactose free facility whereas a product may be ranked least compatible if it was manufactured in a facility that doesn't use lactose as an ingredient but is not a certified lactose free facility. Rankings and order of compatibility may be customized around a user's individual needs whereby one product for a user with celiac disease that is certified gluten free may be highly ranked for one user while that same product may be least compatible for a user with a corn allergy because it is not manufactured in a certified corn free facility.

With continued reference to FIG. 1, system 100 may include a diagnostic engine 128 operating on at least a server 104, wherein the diagnostic engine 128 may be configured to receive at least a biological extraction from a user and generate at least a diagnostic output as a function of the training data and the at least a biological extraction. At least a diagnostic output may include at least a prognostic label and at least an ameliorative process label. At least a server 104, diagnostic engine 128, and/or one or more modules operating thereon may be designed and/or configured to perform any method, method step, or sequence of method steps in any embodiment described in this disclosure, in any order and with any degree of repetition. For instance, at least a server 104 and/or diagnostic engine 128 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. At least a server 104 and/or diagnostic engine 128 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing. Diagnostic engine 128 may be configured to record at least a biological extraction from a user and generate a diagnostic output based on the at least a biological extraction. Diagnostic engine 128 is described in more detail below in reference to FIG. 2.

With continued reference to FIG. 1, system 100 may include a first label learner 132 operating on at least a server 104. First label learner 132 may be designed and configured to select at least a compatible element using a first machine-learning algorithm and the first training data relating physiological data to compatible label 116. At least a first machine-learning model 136 may include one or more models that determine a mathematical relationship between physiological data and compatible label 116. Such models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 1, machine-learning algorithm used to generate first machine-learning model 136 may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 1, first label learner 132 may generate compatibility output using alternatively or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using first training set; the trained network may then be used to apply detected relationships between elements of physiological state data 112 and compatible label 116.

With continued reference to FIG. 1, at least a server 104 may be designed and configured to receive a second training set 140 including a plurality of second data entries. Each second data entry of the second training set 140 includes at least a compatible label 116 and at least a correlated compatible category label 144. Correlation may include any correlation suitable correlation of at least an element of physiological state data 112 and at least a correlated compatible label 116 as described above. Each second data entry of the second training set 140 includes at least a compatible label 116; at least a compatible label 116 may include any label suitable for use as compatible label 116 as described above. As used herein, a compatible category label 144 is a classifier, which identifies compatible products and/or ingredients having particular shared characteristics. Shared characteristics may include traits, and/or qualities that identify a product and/or ingredient as being used for a particular purpose and/or suitable for a particular condition. For example and without limitation, products free of gluten and dairy may contain a compatible category label 144 as indicating products free of gluten and dairy. In yet another non-limiting example, products such as shampoo that are free of gluten and dairy and makeup free of gluten and dairy may contain a compatible category label 144 as indicating personal health care products free of gluten and dairy. In such an instance, a product and/or ingredient may contain a plurality of compatible category label 144, whereby makeup free of gluten and dairy may contain a compatible category label 144 as being free of gluten and dairy allergens, and may contain a second compatible category label 144 as being personal health care products. In yet another non-limiting example, a product such as organic toothpaste that doesn't contain any preservatives or heavy metals and sourced only from plants may contain a compatible category label 144 as indicating being suitable for use by those most at risk for heavy metal toxicity including persons with mercury dental fillings, smokers, and users with chronic autoimmune conditions including hypothyroidism, rheumatoid arthritis, Lupus, multiple sclerosis, and the like. In yet another non-limiting example, clothing that is made from organic cotton may contain a first compatible category label 144 for clothing and a second compatible category label 144 as being compatible for users with skin conditions including contact dermatitis, eczema, and psoriasis. Persons skilled in the art, upon reviewing the entirety of this disclosure, will be aware of various processes that may be used as compatible category label 144 with this disclosure.

Continuing to refer to FIG. 1, in an embodiment at least a server 104 may be configured, for instance as part of receiving second training set 140, to associate a compatible label 116 with at least a category from a list of significant categories of compatible category label 144. This may be performed as described above for use of lists of significant categories with regard to first training set. Significance may be determined, and/or association with at least a category, may be performed for first training set 108 according to a first process as described above and for second training set 140 according to a second process as described above.

Still referring to FIG. 1, at least a server 104 may be configured, for instance as part of receiving second training set 140, to associate at least a correlated compatible category label 144 with at least a category from a list of significant categories of compatible category label 144. In an embodiment, at least a server 104 and/or a user device connected to at least a server 104 may provide a second graphical user interface 148 which may include without limitation a form or other graphical element having data entry fields, wherein one or more experts, including without limitation clinical and/or scientific experts, may enter information describing one or more categories of compatible category label 144 that the experts consider to be significant as described above; fields in graphical user interface may provide options describing previously identified categories, which may include a comprehensive or near-comprehensive list of types of compatible category label 144, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to compatible category label 144, where experts may enter data describing compatible category label 144 and/or categories of compatible category label 144 the experts consider related to entered categories of category labels; for instance, such fields may include drop-down lists or other pre-populated data entry fields listing currently recorded compatible category label 144, and which may be comprehensive, permitting each expert to select a compatible category label 144 and/or a plurality of compatible category label 144 the expert believes to be predicted and/or associated with each category of compatible category label 144 selected by the expert. Fields for entry of compatible category label 144 and/or categories of compatible category label 144 may include free-form data entry fields such as text entry fields; as described above, examiners may enter data not presented in pre-populated data fields in the free-form data entry fields. Alternatively or additionally, fields for entry of compatible category data may enable an expert to select and/or enter information describing or linked to a category of compatible category label 144 that the expert considers significant, where significance may indicate likely impact on longevity, mortality, quality of life, or the like as described in further detail below. Graphical user interface may provide an expert with a field in which to indicate a reference to a document describing significant categories of compatible category label 144, relationships of such categories to user compatible label 116, and/or significant categories of compatible label 116. Such information may alternatively be entered according to any other suitable means for entry of expert data as described above. Data concerning significant categories of compatible category label 144, relationships of such categories to compatible label 116, and/or significant categories of compatible label 116 may be entered using analysis of documents using language processing module 124 or the like as described above.

With continued reference to FIG. 1, at least a server may be configured to receive component elements of training sets and utilize components to generate machine-learning models to select at least a compatible element. Components may include any of the data sets described in first training set, second training set, third training set, and fourth training set. Third and fourth training set are described in more detail below. For example, at least a server may receive components and relate elements between physiological state data 112 and compatible category labels 144.

In an embodiment, and still referring to FIG. 1, at least a server 104 may extract at least a second data entry from one or more documents; extraction may be performed using any language processing method as described above. At least a server 104 may be configured, for instance as part of receiving second training set 140, to receive at least a document describing at least a medical history and extract at least a second data entry of plurality of second data entries from the at least a document. A medical history document may include, for instance, a document received from an expert and/or medical practitioner describing treatment of a patient; document may be anonymized by removal of one or more patient-identifying features from document. A medical history document may include a case study, such as a case study published in a medical journal or written up by an expert. A medical history document may contain data describing and/or described by a compatible label 116; for instance, the medical history document may list a diagnosis that a medical practitioner made concerning the patient, a finding that the patient is at risk for a given condition and/or evinces some precursor state for the condition, or the like and identifies a given product and/or ingredient suitable for use for a given condition. A medical history document may contain data describing and/or described by a compatible category label 144; for instance, the medical history document may list a product, category of product, ingredient recommendation, or other data that a medical practitioner described or recommended to a patient. A medical history document may describe an outcome; for instance, medical history document may describe an improvement in a condition describing or described by a compatible label 116, and/or may describe that the condition did not improve. Compatible label 116 and/or compatible category label 144 may be extracted from and/or determined from one or more medical history documents using any processes for language processing as described above; for instance, language processing module 124 may perform such processes. As a non-limiting example, positive and/or negative indications regarding compatible label 116 identified in medical history documents may be determined in a manner described above for determination of positive and/or negative indications regarding categories of physiological data, relationships of such categories to compatible label 116, and/or categories of compatible label 116.

With continued reference to FIG. 1, at least a server 104 may be configured, for instance as part of receiving second training set 140, to receiving at least a second data entry of the plurality of second data entries from at least an expert. This may be performed, without limitation using second graphical user interface 148 as described above.

With continued reference to FIG. 1, system 100 may include a second label learner 152 operating on the at least a server 104. Second label learner 152 may be designed and configured to select at least a compatible element using a second machine-learning algorithm and the second training set 140. Second label learner 152 may include any hardware or software module suitable for use as first label learner 132 as described above. Second label learner 152 is a machine-learning module as described above; second label learner 152 may perform any machine-learning process or combination of processes suitable for use by first label learner 132 as described above. For instance and without limitation, second label learner 152 may be configured to create a second machine-learning model 156 relating a compatible label 116 to a correlated compatible category label 144. Second machine-learning model 156 may be generated according to any process, process steps, or combination of processes and/or process steps suitable for creation of first machine-learning model 136. In an embodiment, second label learner 152 may use data from first training set 108 as well as data from second training set 140; for instance, second label learner 152 may use lazy learning and/or model generation to determine relationships between elements of physiological data, in combination with or instead of compatible label 116 and compatible category label 144. Where second label learner 152 determines relationships between elements of physiological data and compatible category label 144 directly, this may determine relationships between compatible label 116 and compatible category label 144 as well owing to the existence of relationships determined by first label learner 132.

With continued reference to FIG. 1, at least a server 104 is configured to select at least a compatible element. At least a server 104 may select at least a compatible element as a function of at least a compatible element category. At least a compatible element category as used herein is an element of data which identifies a compatible element having particular shared characteristics. Shared characteristics may include traits, and/or qualities that identify a compatible element as being uses for a particular purpose and/or being used for a particular condition. At least a compatible element category may include a description identifying a compatible element as being used for a particular purpose. For example, a compatible element such as a television may be labeled with a compatible element category such as "electronic" while a compatible element such as body wash may be labeled with a compatible element category such as "health and personal care." In yet another non-limiting example, a compatible element such as a food product may be labeled with a compatible element category such as "grocery & gourmet food" while a compatible element such as hiking boots may be labeled with a compatible element category such as "outdoors." In an embodiment, a compatible element may contain a plurality of compatible element categories, for example a toaster oven may be labeled with a first compatible element category such as "electronic" and with a second compatible element category such as "kitchenware."

With continued reference to FIG. 1, at least a server 104 may select at least a compatible element as a function of a previous user activity. Previous user activity may include any previous interactions that a user may have had with system 100. In an embodiment, a user who previously selected and/or purchased a compatible element such as a particular brand of body wash may have that same compatible element selected by at least a server 104. In yet another non-limiting example, previously user activity such as a previously selected and/or purchased compatible element may be used to select at least a compatible element having shared traits such as same manufacturer or as being a compatible element that was also selected and/or purchased by other users who purchased the same original compatible element. For example, previous user activity that shows a user browsing all body products produced by a particular manufacturer may be utilized to select at least a compatible element manufactured by the same manufacturer. In yet another non-limiting example, previous user activity that shows a user browsing all hair products produced by a particular manufacturer may be utilized to select at least a compatible element such as a body wash manufactured by a company that uses similar manufacturing standards and similar ingredients as the hair products but that is out of stock of body wash or doesn't manufacture body wash.

With continued reference to FIG. 1, at least a server 104 may be configured to select at least a first compatible element by retrieving at least a compatible element index value from a database and select at least a compatible element as a function of the compatible element index. Compatible element index as used herein, is a value assigned to a compatible element indicating a degree of similarity between a first compatible element and a second compatible element. In an embodiment, compatible element index scores may be stored in a database or datastore as described below in more detail in reference to FIG. 11. In an embodiment, a compatible element index may be calculated based on correlations between past user purchase history, past overall purchase history, and similarity of products and/or product ingredients. In an embodiment, compatible element index may be ranked whereby a high compatible element index between any two compatible elements may indicate that for any two compatible elements a large percentage of users who browsed, selected, and/or purchased a first compatible element then browsed, selected, and/or purchased a second compatible element. A low compatible element index between any two compatible elements may indicate that for any two compatible elements a small percentage of users who browsed, selected, and/or purchased a first compatible element then browsed, selected, and/or purchased a second compatible element. In an embodiment, compatible element index may be utilized to generate a compatible element index list that may be generated for a given compatible element by selecting N other compatible elements that have the highest compatible element index number and including those compatible elements on the compatible element index list. Compatible element index is described below in more detail in reference to FIG. 11.

With continued reference to FIG. 1, at least a server 104 may be configured to select at least a first compatible element by retrieving at least a compatible element physiological index value from a database and selecting at least a compatible element as a function of the physiological index value. Physiological index value as used herein, is a value assigned to a compatible element indicating a degree of similarity between the effect of a first product and a second product on a user with a particular element of physiological data. Similarity may include how closely any second compatible element can be substituted for a first compatible element as a function of a user's physiological data and/or biological extraction. In an embodiment, a second compatible element may be substituted for a first compatible element such as when the first compatible element is unavailable, on backorder, too expensive for a user, costs too much to ship to a user and/or any of reason that may affect a user being able to obtain first compatible element. In an embodiment, a second compatible element may be selected so as to suggest to a user another product and/or ingredient that user may wish to use and/or purchase. For example, physiological index value may provide information describing how easily one brand of a shampoo intended for a user with eczema can be substituted for a second brand of shampoo intended for the same user with eczema. In yet another non-limiting example, physiological index value may provide information describing how easily one brand of mouthwash can be substituted for a first brand of shampoo intended for a user with burning mouth syndrome. In yet another non-limiting example, physiological index value may provide information describing how easily one nutraceutical can be substituted for a first nutraceutical for a patient with a methylenetetrahydrofolate reductase mutation. In yet another non-limiting example, a first product that is free of gluten may be compatible for a user with Celiac Disease while a second product may not be compatible for a user with Celiac Disease because it contains traces of wheat or barley. In an embodiment, physiological index value scores may be stored in a database or datastore as described below in more detail in reference to FIG. 12. In an embodiment, a physiological index value score may be calculated based on correlations between past user purchase history, past overall purchase history, and similarity of products and/or product ingredients. In an embodiment, physiological index value score may be ranked whereby a high physiological index score between any two compatible elements may indicate that a second compatible element can be substituted for a first compatible element for a user possessing a particular physiological trait such as a user with a mutation of the SRD5A2 gene or a user with a mutation of the BCMO1 gene. A low physiological index score between any two compatible elements may indicate that a second compatible element cannot be substituted for a first compatible element for a user possessing a particular physiological trait such as a gene mutation or predisposition to develop a medical condition such as prediabetes or gout. In an embodiment, compatibility index may be utilized to generate a physiological index list that may be generated for a given compatible element by selecting N other compatible elements that have the highest physiological index scores and including those compatible elements on the physiological index list. Physiological index is described below in more detail in reference to FIG. 12.

With continued reference to FIG. 1, at least a server 104 is configured to transmit the at least a compatible element to a user client device 160. A user client device 160 may include, without limitation, a display in communication with at least a server 104; display may include any display as described herein. A user client device 160 may include an additional computing device, such as a mobile device, laptop, desktop computer, or the like; as a non-limiting example, the user client device 160 may be a computer and/or workstation operated by a medical professional. Output may be displayed on at least a user client device 160 using an output graphical user interface, as described in more detail below. Transmission to a user client device 160 may include any of the transmission methodologies as described herein.

Figure 2:
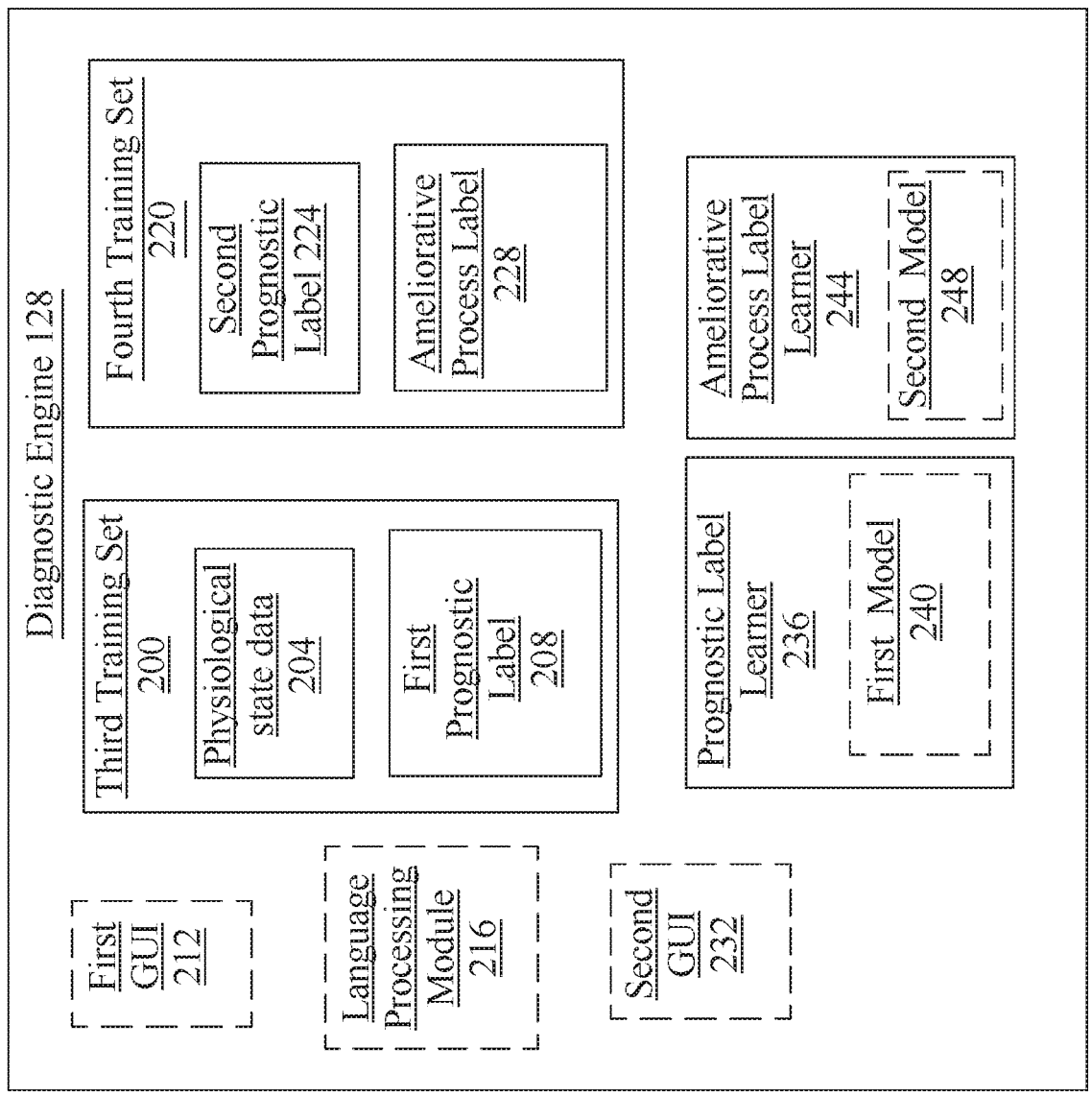
FIG. 2 is a block diagram illustrating an exemplary embodiment of a diagnostic engine.

Referring now to FIG. 2, an exemplary embodiment of diagnostic engine 128 is illustrated. In an embodiment, diagnostic engine 128 may be configured to record at least a biological extraction from a user and generate a diagnostic output based on the at least a biological extraction. At least a biological extraction may include any of the biological extractions as described above in reference to FIG. 1. In an embodiment, diagnostic engine 128 may generate a diagnostic output based on the at least a biological extraction using training data and a machine-learning model. Training data may include any of the training data as described above in reference to FIG. 1. In an embodiment, diagnostic engine 128 may receive a third training set 200 including a plurality of first data entries, each first data entry of the third training set 200 including at least an element of physiological state data 204 and at least a correlated first prognostic label 208. Physiological state data 204 may include any of the physiological state data 112 as described above in reference to FIG. 1.

Continuing to refer to FIG. 2, each element of third training set 200 includes at least a first prognostic label 208. A prognostic label, as described herein, is an element of data identifying and/or describing a current, incipient, or probable future medical condition affecting a person; medical condition may include a particular disease, one or more symptoms associated with a syndrome, a syndrome, and/or any other measure of current or future health and/or heathy aging. At least a prognostic label may be associated with a physical and/or somatic condition, a mental condition such as a mental illness, neurosis, or the like, or any other condition affecting human health that may be associated with one or more elements of physiological state data 204 as described in further detail below. Conditions associated with prognostic labels may include, without limitation one or more diseases, defined for purposes herein as conditions that negatively affect structure and/or function of part or all of an organism. Conditions associated with prognostic labels may include, without limitation, acute or chronic infections, including without limitation infections by bacteria, archaea, viruses, viroids, prions, single-celled eukaryotic organisms such as amoeba, paramecia, trypanosomes, plasmodia, leishmania, and/or fungi, and/or multicellular parasites such as nematodes, arthropods, fungi, or the like. Prognostic labels may be associated with one or more immune disorders, including without limitation immunodeficiencies and/or auto-immune conditions. Prognostic labels may be associated with one or more metabolic disorders. Prognostic labels may be associated with one or more endocrinal disorders. Prognostic labels may be associated with one or more cardiovascular disorders. Prognostic labels may be associated with one or more respiratory disorders. Prognostic labels may be associated with one or more disorders affecting connective tissue. Prognostic labels may be associated with one or more digestive disorders. Prognostic labels may be associated with one or more neurological disorders such as neuromuscular disorders, dementia, or the like. Prognostic labels may be associated with one or more disorders of the excretory system, including without limitation nephrological disorders. Prognostic labels may be associated with one or more liver disorders. Prognostic labels may be associated with one or more disorders of the bones such as osteoporosis. Prognostic labels may be associated with one or more disorders affecting joints, such as osteoarthritis, gout, and/or rheumatoid arthritis. Prognostic labels be associated with one or more cancers, including without limitation carcinomas, lymphomas, leukemias, germ cell tumor cancers, blastomas, and/or sarcomas. Prognostic labels may include descriptors of latent, dormant, and/or apparent disorders, diseases, and/or conditions. Prognostic labels may include descriptors of conditions for which a person may have a higher than average probability of development, such as a condition for which a person may have a "risk factor"; for instance, a person currently suffering from abdominal obesity may have a higher than average probability of developing type II diabetes. The above-described examples are presented for illustrative purposes only and are not intended to be exhaustive. Persons skilled in the art, upon reviewing the entirety of this disclosure, will be aware of various additional examples of conditions that may be associated with prognostic labels as described in this disclosure.

Still referring to FIG. 2, at least a prognostic label may be stored in any suitable data and/or data type. For instance, and without limitation, at least a prognostic label may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as at least a prognostic label may take; persons skilled in the art, upon reviewing the entirety of this disclosure, will be aware of various forms which may be suitable for use as at least a prognostic label consistently with this disclosure.

With continued reference to FIG. 2, in each first data element of third training set 200, at least a first prognostic label 208 of the data element is correlated with at least an element of physiological state data 204 of the data element. In an embodiment, an element of physiological data is correlated with a prognostic label where the element of physiological data is located in the same data element and/or portion of data element as the prognostic label; for example, and without limitation, an element of physiological data is correlated with a prognostic element where both element of physiological data and prognostic element are contained within the same first data element of the third training set 200. As a further example, an element of physiological data is correlated with a prognostic element where both share a category label as described in further detail below, where each is within a certain distance of the other within an ordered collection of data in data element, or the like. Still further, an element of physiological data may be correlated with a prognostic label where the element of physiological data and the prognostic label share an origin, such as being data that was collected with regard to a single person or the like. In an embodiment, a first datum may be more closely correlated with a second datum in the same data element than with a third datum contained in the same data element; for instance, the first element and the second element may be closer to each other in an ordered set of data than either is to the third element, the first element and second element may be contained in the same subdivision and/or section of data while the third element is in a different subdivision and/or section of data, or the like. Persons skilled in the art, upon reviewing the entirety of this disclosure, will be aware of various forms and/or degrees of correlation between physiological data and prognostic labels that may exist in first training set 108 and/or first data element consistently with this disclosure.

In an embodiment, and still referring to FIG. 2, diagnostic engine 128 may be designed and configured to associate at least an element of physiological state data 204 with at least a category from a list of significant categories of physiological state data 204. Significant categories of physiological state data 204 may include labels and/or descriptors describing types of physiological state data 204 that are identified as being of high relevance in identifying prognostic labels. As a non-limiting example, one or more categories may identify significant categories of physiological state data 204 based on degree of diagnostic relevance to one or more impactful conditions and/or within one or more medical or public health fields. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss. As an additional example, hemoglobin levels may be useful for identifying elevated testosterone, poor oxygen deliverability, thiamin deficiency, insulin resistance, anemia, liver disease, hypothyroidism, arginine deficiency, protein deficiency, inflammation, and/or nutrient deficiencies. In a further non-limiting example, hematocrit may be useful for identifying dehydration, elevated testosterone, poor oxygen deliverability, thiamin deficiency, insulin resistance, anemia, liver disease, hypothyroidism, arginine deficiency, protein deficiency, inflammation, and/or nutrient deficiencies. Similarly, measures of lipid levels in blood, such as total cholesterol, HDL, LDL, VLDL, triglycerides, LDL-C and/or HDL-C may be recognized as useful in identifying conditions such as poor thyroid function, insulin resistance, blood glucose dysregulation, magnesium deficiency, dehydration, kidney disease, familial hypercholesterolemia, liver dysfunction, oxidative stress, inflammation, malabsorption, anemia, alcohol abuse, diabetes, hypercholesterolemia, coronary artery disease, atherosclerosis, or the like. Persons skilled in the art, upon reviewing the entirety of this disclosure, will be aware of various additional categories of physiological data that may be used consistently with this disclosure.

Still referring to FIG. 2, diagnostic engine 128 may receive the list of significant categories according to any suitable process; for instance, and without limitation, diagnostic engine 128 may receive the list of significant categories from at least an expert. In an embodiment, diagnostic engine 128 and/or a user device connected to diagnostic engine 128 may provide a graphical user interface, which may include without limitation a form or other graphical element having data entry fields, wherein one or more experts, including without limitation clinical and/or scientific experts, may enter information describing one or more categories of physiological data that the experts consider to be significant or useful for detection of conditions; fields in graphical user interface may provide options describing previously identified categories, which may include a comprehensive or near-comprehensive list of types of physiological data detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to prognostic labels, where experts may enter data describing prognostic labels and/or categories of prognostic labels the experts consider related to entered categories of physiological data; for instance, such fields may include drop-down lists or other pre-populated data entry fields listing currently recorded prognostic labels, and which may be comprehensive, permitting each expert to select a prognostic label and/or a plurality of prognostic labels the expert believes to be predicted and/or associated with each category of physiological data selected by the expert. Fields for entry of prognostic labels and/or categories of prognostic labels may include free-form data entry fields such as text entry fields; as described above, examiners may enter data not presented in pre-populated data fields in the free-form data entry fields. Alternatively or additionally, fields for entry of prognostic labels may enable an expert to select and/or enter information describing or linked to a category of prognostic label that the expert considers significant, where significance may indicate likely impact on longevity, mortality, quality of life, or the like as described in further detail below. Graphical user interface may provide an expert with a field in which to indicate a reference to a document describing significant categories of physiological data, relationships of such categories to prognostic labels, and/or significant categories of prognostic labels. Any data described above may alternatively or additionally be received from experts similarly organized in paper form, which may be captured and entered into data in a similar way, or in a textual form such as a portable document file (PDF) with examiner entries, or the like.

With continued reference to FIG. 2, data information describing significant categories of physiological data, relationships of such categories to prognostic labels, and/or significant categories of prognostic labels may alternatively or additionally be extracted from one or more documents using a language processing module 216. Language processing module 216 may include any hardware and/or software module. Language processing module 216 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 2, language processing module 216 may compare extracted words to categories of physiological data recorded at diagnostic engine 128, one or more prognostic labels recorded at diagnostic engine 128, and/or one or more categories of prognostic labels recorded at diagnostic engine 128; such data for comparison may be entered on diagnostic engine 128 as described above using expert data inputs or the like. In an embodiment, one or more categories may be enumerated, to find total count of mentions in such documents. Alternatively or additionally, language processing module 216 may operate to produce a language processing model. Language processing model may include a program automatically generated by diagnostic engine 128 and/or language processing module 216 to produce associations between one or more words extracted from at least a document and detect associations, including without limitation mathematical associations, between such words, and/or associations of extracted words with categories of physiological data, relationships of such categories to prognostic labels, and/or categories of prognostic labels. Associations between language elements, where language elements include for purposes herein extracted words, categories of physiological data, relationships of such categories to prognostic labels, and/or categories of prognostic labels may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to prognostic labels, and/or a given category of prognostic labels. As a further example, statistical correlations and/or mathematical associations may include probabilistic formulas or relationships indicating a positive and/or negative association between at least an extracted word and/or a given category of physiological data, a given relationship of such categories to prognostic labels, and/or a given category of prognostic labels; positive or negative indication may include an indication that a given document is or is not indicating a category of physiological data, relationship of such category to prognostic labels, and/or category of prognostic labels is or is not significant. For instance, and without limitation, a negative indication may be determined from a phrase such as "telomere length was not found to be an accurate predictor of overall longevity," whereas a positive indication may be determined from a phrase such as "telomere length was found to be an accurate predictor of dementia," as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at diagnostic engine 128, or the like.

Still referring to FIG. 2, language processing module 216 and/or diagnostic engine 128 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs has used herein are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HMM inference algorithm, such as the forward-backward algorithm or the Viterbi algorithm, may be used to estimate the most likely discrete state given a word or sequence of words. Language processing module 216 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

With continued reference to FIG. 2, at least a server 104 and/or diagnostic engine 112 may be configured to receive component elements of training sets and utilize components to generate machine-learning models to select at least a compatible element. Components may include any of the data sets described in first training set, second training set, third training set, and fourth training set. For example, at least a server may receive components and relate elements between first prognostic label 208 and compatible label 116 or compatible category labels 144 using machine-learning models as described herein. In yet another non-limiting example, at least a server 104 and/or diagnostic engine 112 may relate elements between ameliorative process label 228 and compatible label 116 or ameliorative process label 228 and compatible category label 144. In yet another non-limiting example, at least a server 104 and/or diagnostic engine 112 may relate elements between diagnostic outputs and compatible label 116 or diagnostic output and compatible category label 144.

Continuing to refer to FIG. 2, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 2, language processing module 216 may use a corpus of documents to generate associations between language elements in a language processing module 216, and diagnostic engine 128 may then use such associations to analyze words extracted from one or more documents and determine that the one or more documents indicate significance of a category of physiological data, a given relationship of such categories to prognostic labels, and/or a given category of prognostic labels. In an embodiment, diagnostic engine 128 may perform this analysis using a selected set of significant documents, such as documents identified by one or more experts as representing good science, good clinical analysis, or the like; experts may identify or enter such documents via graphical user interface as described above in reference to FIG. 9, or may communicate identities of significant documents according to any other suitable method of electronic communication, or by providing such identity to other persons who may enter such identifications into diagnostic engine 128. Documents may be entered into diagnostic engine 128 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, diagnostic engine 128 may automatically obtain the document using such an identifier, for instance by submitting a request to a database or compendium of documents such as JSTOR as provided by Ithaka Harbors, Inc. of New York.

Continuing to refer to FIG. 2, whether an entry indicating significance of a category of physiological data, a given relationship of such categories to prognostic labels, and/or a given category of prognostic labels is entered via graphical user interface, alternative submission means, and/or extracted from a document or body of documents as described above, an entry or entries may be aggregated to indicate an overall degree of significance. For instance, each category of physiological data, relationship of such categories to prognostic labels, and/or category of prognostic labels may be given an overall significance score; overall significance score may, for instance, be incremented each time an expert submission and/or paper indicates significance as described above. Persons skilled in the art, upon reviewing the entirety of this disclosure will be aware of other ways in which scores may be generated using a plurality of entries, including averaging, weighted averaging, normalization, and the like. Significance scores may be ranked; that is, all categories of physiological data, relationships of such categories to prognostic labels, and/or categories of prognostic labels may be ranked according to significance scores, for instance by ranking categories of physiological data, relationships of such categories to prognostic labels, and/or categories of prognostic labels higher according to higher significance scores and lower according to lower significance scores. Categories of physiological data, relationships of such categories to prognostic labels, and/or categories of prognostic labels may be eliminated from current use if they fail a threshold comparison, which may include a comparison of significance score to a threshold number, a requirement that significance score belong to a given portion of ranking such as a threshold percentile, quartile, or number of top-ranked scores. Significance scores may be used to filter outputs as described in further detail below; for instance, where a number of outputs are generated and automated selection of a smaller number of outputs is desired, outputs corresponding to higher significance scores may be identified as more probable and/or selected for presentation while other outputs corresponding to lower significance scores may be eliminated. Alternatively or additionally, significance scores may be calculated per sample type; for instance, entries by experts, documents, and/or descriptions of purposes of a given type of physiological test or sample collection as described above may indicate that for that type of physiological test or sample collection a first category of physiological data, relationship of such category to prognostic labels, and/or category of prognostic labels is significant with regard to that test, while a second category of physiological data, relationship of such category to prognostic labels, and/or category of prognostic labels is not significant; such indications may be used to perform a significance score for each category of physiological data, relationship of such category to prognostic labels, and/or category of prognostic labels is or is not significant per type of biological extraction, which then may be subjected to ranking, comparison to thresholds and/or elimination as described above.

Still referring to FIG. 2, diagnostic engine 128 may detect further significant categories of physiological data, relationships of such categories to prognostic labels, and/or categories of prognostic labels using machine-learning processes, including without limitation unsupervised machine-learning processes as described in further detail below; such newly identified categories, as well as categories entered by experts in free-form fields as described above, may be added to pre-populated lists of categories, lists used to identify language elements for language learning module, and/or lists used to identify and/or score categories detected in documents, as described above.

Continuing to refer to FIG. 2, in an embodiment, diagnostic engine 128 may be configured, for instance as part of receiving the third training set 200, to associate at least correlated first prognostic label 208 with at least a category from a list of significant categories of prognostic labels. Significant categories of prognostic labels may be acquired, determined, and/or ranked as described above. As a non-limiting example, prognostic labels may be organized according to relevance to and/or association with a list of significant conditions. A list of significant conditions may include, without limitation, conditions having generally acknowledged impact on longevity and/or quality of life; this may be determined, as a non-limiting example, by a product of relative frequency of a condition within the population with years of life and/or years of able-bodied existence lost, on average, as a result of the condition. A list of conditions may be modified for a given person to reflect a family history of the person; for instance, a person with a significant family history of a particular condition or set of conditions, or a genetic profile having a similarly significant association therewith, may have a higher probability of developing such conditions than a typical person from the general population, and as a result diagnostic engine 128 may modify list of significant categories to reflect this difference.

Still referring to FIG. 2, diagnostic engine 128 is designed and configured to receive a fourth training set 220 including a plurality of second data entries. Each second data entry of the fourth training set 220 includes at least a second prognostic label 224; at least a second prognostic label 224 may include any label suitable for use as at least a first prognostic label 208 as described above. Each second data entry of the fourth training set 220 includes at least an ameliorative process label 228 correlated with the at least a second prognostic label 224, where correlation may include any correlation suitable for correlation of at least a first prognostic label 208 to at least an element of physiological data as described above. As used herein, an ameliorative process label 228 is an identifier, which may include any form of identifier suitable for use as a prognostic label as described above, identifying a process that tends to improve a physical condition of a user, where a physical condition of a user may include, without limitation, any physical condition identifiable using a prognostic label. Ameliorative processes may include, without limitation, exercise programs, including amount, intensity, and/or types of exercise recommended. Ameliorative processes may include, without limitation, dietary or nutritional recommendations based on data including nutritional content, digestibility, or the like. Ameliorative processes may include one or more medical procedures. Ameliorative processes may include one or more physical, psychological, or other therapies. Ameliorative processes may include one or more medications. Persons skilled in the art, upon reviewing the entirety of this disclosure, will be aware of various processes that may be used as ameliorative processes consistently with this disclosure.

Continuing to refer to FIG. 2, in an embodiment diagnostic engine 128 may be configured, for instance as part of receiving fourth training set 220, to associate the at least second prognostic label 224 with at least a category from a list of significant categories of prognostic labels. This may be performed as described above for use of lists of significant categories with regard to at least a first prognostic label 208. Significance may be determined, and/or association with at least a category, may be performed for prognostic labels in first training set 108 according to a first process as described above and for prognostic labels in fourth training set 220 according to a second process as described above.

Still referring to FIG. 2, diagnostic engine 128 may be configured, for instance as part of receiving fourth training set 220, to associate at least a correlated ameliorative process label 228 with at least a category from a list of significant categories of ameliorative process labels 228. In an embodiment, diagnostic engine 128 and/or a user device connected to diagnostic engine 128 may provide a second graphical user interface 232 which may include without limitation a form or other graphical element having data entry fields, wherein one or more experts, including without limitation clinical and/or scientific experts, may enter information describing one or more categories of prognostic labels that the experts consider to be significant as described above; fields in graphical user interface may provide options describing previously identified categories, which may include a comprehensive or near-comprehensive list of types of prognostic labels, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to ameliorative labels, where experts may enter data describing ameliorative labels and/or categories of ameliorative labels the experts consider related to entered categories of prognostic labels; for instance, such fields may include drop-down lists or other pre-populated data entry fields listing currently recorded ameliorative labels, and which may be comprehensive, permitting each expert to select an ameliorative label and/or a plurality of ameliorative labels the expert believes to be predicted and/or associated with each category of prognostic labels selected by the expert. Fields for entry of ameliorative labels and/or categories of ameliorative labels may include free-form data entry fields such as text entry fields; as described above, examiners may enter data not presented in pre-populated data fields in the free-form data entry fields. Alternatively or additionally, fields for entry of ameliorative labels may enable an expert to select and/or enter information describing or linked to a category of ameliorative label that the expert considers significant, where significance may indicate likely impact on longevity, mortality, quality of life, or the like as described in further detail below. Graphical user interface may provide an expert with a field in which to indicate a reference to a document describing significant categories of prognostic labels, relationships of such categories to ameliorative labels, and/or significant categories of ameliorative labels. Such information may alternatively be entered according to any other suitable means for entry of expert data as described above. Data concerning significant categories of prognostic labels, relationships of such categories to ameliorative labels, and/or significant categories of ameliorative labels may be entered using analysis of documents using language processing module 216 or the like as described above.

In an embodiment, and still referring to FIG. 2, diagnostic engine 128 may extract at least a second data entry from one or more documents; extraction may be performed using any language processing method as described above. Diagnostic engine 128 may be configured, for instance as part of receiving fourth training set 220, to receive at least a document describing at least a medical history and extract at least a second data entry of plurality of second data entries from the at least a document. A medical history document may include, for instance, a document received from an expert and/or medical practitioner describing treatment of a patient; document may be anonymized by removal of one or more patient-identifying features from document. A medical history document may include a case study, such as a case study published in a medical journal or written up by an expert. A medical history document may contain data describing and/or described by a prognostic label; for instance, the medical history document may list a diagnosis that a medical practitioner made concerning the patient, a finding that the patient is at risk for a given condition and/or evinces some precursor state for the condition, or the like. A medical history document may contain data describing and/or described by an ameliorative process label 228; for instance, the medical history document may list a therapy, recommendation, or other ameliorative process that a medical practitioner described or recommended to a patient. A medical history document may describe an outcome; for instance, medical history document may describe an improvement in a condition describing or described by a prognostic label, and/or may describe that the condition did not improve. Prognostic labels, ameliorative process labels 228, and/or efficacy of ameliorative process labels 228 may be extracted from and/or determined from one or more medical history documents using any processes for language processing as described above; for instance, language processing module 216 may perform such processes. As a non-limiting example, positive and/or negative indications regarding ameliorative processes identified in medical history documents may be determined in a manner described above for determination of positive and/or negative indications regarding categories of physiological data, relationships of such categories to prognostic labels, and/or categories of prognostic labels.

With continued reference to FIG. 2, diagnostic engine 128 may be configured, for instance as part of receiving fourth training set 220, to receiving at least a second data entry of the plurality of second data entries from at least an expert. This may be performed, without limitation using second graphical user interface 148 as described above.

With continued reference to FIG. 2, diagnostic engine 128 may include a prognostic label learner 236 operating on the diagnostic engine 128, the prognostic label learner 236 designed and configured to generate the at least a prognostic output as a function of the third training set 200 and the at least a biological extraction. Prognostic label learner 236 may include any hardware and/or software module. Prognostic label learner 236 is designed and configured to generate outputs using machine learning processes. A machine learning process is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language.

Still referring to FIG. 2, prognostic label learner 236 may be designed and configured to generate at least a prognostic output by creating at least a first machine-learning model 240 relating physiological state data 204 to prognostic labels using the third training set 200 and generating the at least a prognostic output using the first machine-learning model 240; at least a first machine-learning model 240 may include one or more models that determine a mathematical relationship between physiological state data 204 and prognostic labels. Such models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithm used to generate first machine-learning model 240 may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, prognostic label learner 236 may generate prognostic output using alternatively or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using third training set 200; the trained network may then be used to apply detected relationships between elements of physiological state data 204 and prognostic labels.

Figure 3:
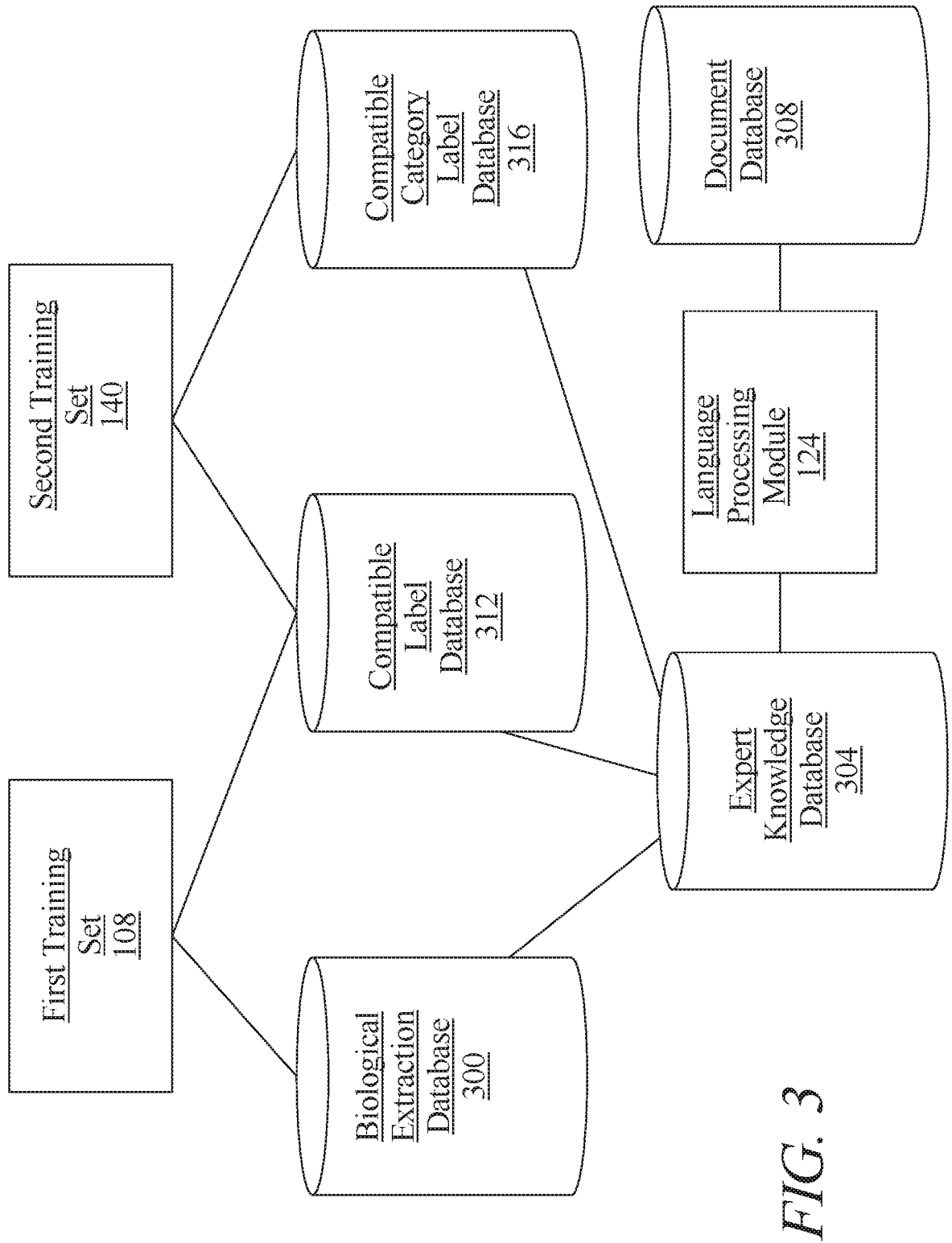
FIG. 3 is a block diagram illustrating embodiments of data storage facilities for use in disclosed systems and methods.

Referring now to FIG. 3, data incorporated in first training set 108 and/or second training set 140 may be incorporated in one or more databases. As a non-limiting example, one or elements of physiological data may be stored in and/or retrieved from a biological extraction database 300. A biological extraction database 300 may include any data structure for ordered storage and retrieval of data, which may be implemented as a hardware or software module. A biological extraction database 300 may be implemented, without limitation, as a relational database, a key-value retrieval datastore such as a NOSQL database, or any other format or structure for use as a datastore that a person skilled in the art would recognize as suitable upon review of the entirety of this disclosure. A biological extraction database 300 may include a plurality of data entries and/or records corresponding to elements of physiological data as described above. Data entries and/or records may describe, without limitation, data concerning particular biological extractions that have been collected; entries may describe reasons for collection of samples, such as without limitation one or more conditions being tested for, which may be listed with related compatible label 116. Data entries may include compatible label 116 and/or other descriptive entries describing results of evaluation of past biological extractions, including diagnoses that were associated with such samples, prognoses and/or conclusions regarding likelihood of future diagnoses that were associated with such samples, and/or other medical or diagnostic conclusions that were derived. Such conclusions may have been generated by diagnostic engine 128 in previous iterations of methods, with or without validation of correctness by medical professionals. Data entries in a biological extraction database 300 may be flagged with or linked to one or more additional elements of information, which may be reflected in data entry cells and/or in linked tables such as tables related by one or more indices in a relational database; one or more additional elements of information may include data associating a biological extraction and/or a person from whom a biological extraction was extracted or received with one or more cohorts, including demographic groupings such as ethnicity, sex, age, income, geographical region, or the like, one or more common diagnoses or physiological attributes shared with other persons having biological extractions reflected in other data entries, or the like. Additional elements of information may include one or more categories of physiological data as described above. Additional elements of information may include descriptions of particular methods used to obtain biological extractions, such as without limitation physical extraction of blood samples or the like, capture of data with one or more sensors, and/or any other information concerning provenance and/or history of data acquisition. Persons skilled in the art, upon reviewing the entirety of this disclosure, will be aware of various ways in which data entries in a biological extraction database 300 may reflect categories, cohorts, and/or populations of data consistently with this disclosure.

With continued reference to FIG. 3, at least a server 104 and/or another device in communication with at least a server 104 may populate one or more fields in biological extraction database 300 using expert information, which may be extracted or retrieved from an expert knowledge database 304. An expert knowledge database 304 may include any data structure and/or data store suitable for use as a biological extraction database 300 as described above. Expert knowledge database 304 may include data entries reflecting one or more expert submissions of data such as may have been submitted according to any process described above in reference to FIGS. 1-2 including without limitation by using first graphical user interface 120 and/or second graphical user interface 148. Expert knowledge database may include one or more fields generated by language processing module 124, such as without limitation fields extracted from one or more documents as described above. For instance, and without limitation, one or more categories of physiological data and/or related compatible label 116 and/or categories of compatible label 116 associated with an element of physiological state data 112 as described above may be stored in generalized from in an expert knowledge database 304 and linked to, entered in, or associated with entries in a biological extraction database 300. Documents may be stored and/or retrieved by at least a server 104 and/or language processing module 124 in and/or from a document database 308; document database 308 may include any data structure and/or data store suitable for use as biological extraction database 300 as described above. Documents in document database 308 may be linked to and/or retrieved using document identifiers such as URI and/or URL data, citation data, or the like; persons skilled in the art, upon reviewing the entirety of this disclosure, will be aware of various ways in which documents may be indexed and retrieved according to citation, subject matter, author, date, or the like as consistent with this disclosure.

With continued reference to FIG. 3, a compatible label database 312, which may be implemented in any manner suitable for implementation of biological extraction database 300, may be used to store compatible labels used by at least a server 104, including any compatible label 116 correlated with elements of physiological data in first training set 108 as described above; compatible label 116 may be linked to or refer to entries in biological extraction database 300 to which compatible label 116 correspond. Linking may be performed by reference to historical data concerning biological extractions, such as diagnoses, prognoses, and/or other medical conclusions derived from biological extractions in the past; alternatively or additionally, a relationship between a compatible label 116 and a data entry in biological extraction database 300 may be determined by reference to a record in an expert knowledge database 304 linking a given compatible label 116 to a given category of biological extraction as described above. Entries in compatible label database 312 may be associated with one or more categories of compatible label 116 as described above, for instance using data stored in and/or extracted from an expert knowledge database 304.

With continued reference to FIG. 3, first training set 108 may be populated by retrieval of one or more records from biological extraction database 300 and/or compatible label database 312; in an embodiment, entries retrieved from biological extraction database 300 and/or compatible label database 312 may be filtered and or select via query to match one or more additional elements of information as described above, so as to retrieve a first training set 108 including data belonging to a given cohort, demographic population, or other set, so as to generate outputs as described below that are tailored to a person or persons with regard to whom at least a server 104 classifies biological extractions to compatible label 116 as set forth in further detail below. Persons skilled in the art, upon reviewing the entirety of this disclosure, will be aware of various ways in which records may be retrieved from biological extraction database 300 and/or compatible label 116 database to generate a first training set 108 to reflect individualized group data pertaining to a person of interest in operation of system and/or method, including without limitation a person with regard to whom at least a biological extraction is being evaluated as described in further detail below. At least a server 104 may alternatively or additionally receive a first training set 108 and store one or more entries in biological extraction database 300 and/or compatible label database 312 as extracted from elements of first training set.

Still referring to FIG. 3, at least a server 104 may include or communicate with a compatible category label database 316; a compatible category label database 316 may include any data structure and/or datastore suitable for use as a biological extraction database 300 as described above. A compatible category label database 316 may include one or more entries listing labels associated with one or more user input datums as described above, including any user input datums correlated with compatible category label 144 in second training set 140 as described above; user input labels may be linked to or refer to entries in compatible label database 312 to which user input labels correspond. Linking may be performed by reference to historical data concerning compatible label 116, such as therapies, treatments, and/or lifestyle or dietary choices chosen to alleviate conditions associated with compatible label 116 in the past; alternatively or additionally, a relationship between a compatible category label 144 and a data entry in compatible label database 312 may be determined by reference to a record in an expert knowledge database 304 linking a given compatible category label 144 to a given category of compatible label 116 as described above. Entries in compatible label database 312 may be associated with one or more categories of compatible label 116 as described above, for instance using data stored in and/or extracted from an expert knowledge database 304.

Figure 4:
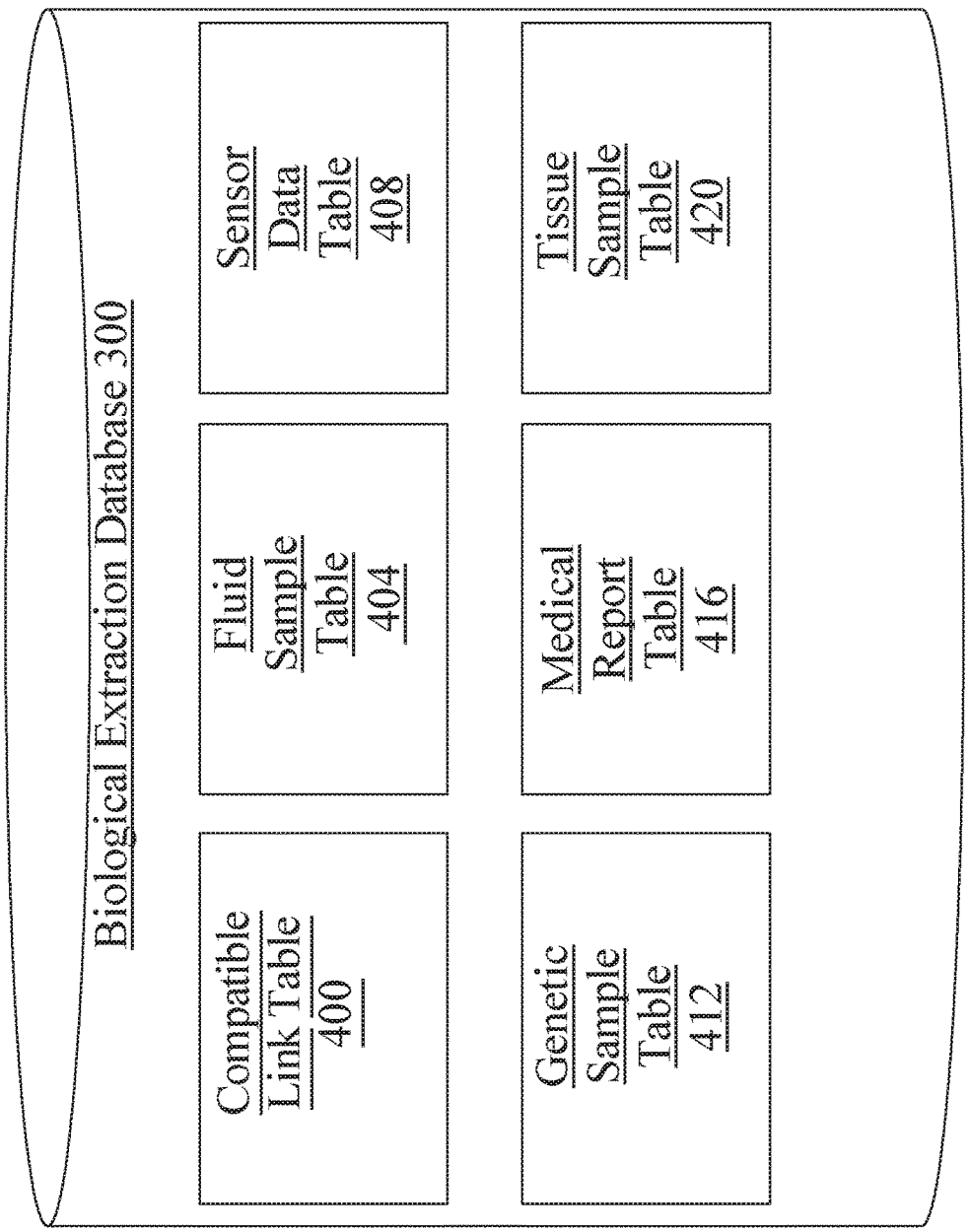
FIG. 4 is a block diagram illustrating an exemplary embodiment of a biological extraction database.

Referring now to FIG. 4, one or more database tables in biological extraction database 300 may include, as a non-limiting example, a compatible link table 400. Compatible link table 400 may be a table relating biological extraction data as described above to compatible label 116; for instance, where an expert has entered data relating a compatible label to a category of biological extraction data and/or to an element of biological extraction data via first graphical user interface 120 as described above, one or more rows recording such an entry may be inserted in compatible link table 400. Alternatively or additionally, linking of compatible label 116 to biological extraction data may be performed entirely in compatible label database as described below.

With continued reference to FIG. 4, biological extraction database 300 may include tables listing one or more samples according to sample source. For instance, and without limitation, biological extraction database 300 may include a fluid sample table 404 listing samples acquired from a person by extraction of fluids, such as without limitation blood, lymph cerebrospinal fluid, or the like. As another non-limiting example, biological extraction database 300 may include a sensor data table 408, which may list samples acquired using one or more sensors, for instance as described in further detail below. As a further non-limiting example, biological extraction database 300 may include a genetic sample table 412, which may list partial or entire sequences of genetic material. Genetic material may be extracted and amplified, as a non-limiting example, using polymerase chain reactions (PCR) or the like. As a further example, also non-limiting, biological extraction database 300 may include a medical report table 416, which may list textual descriptions of medical tests, including without limitation radiological tests or tests of strength and/or dexterity or the like. Data in medical report table may be sorted and/or categorized using a language processing module 124, for instance, translating a textual description into a numerical value and a label corresponding to a category of physiological data; this may be performed using any language processing algorithm or algorithms as referred to in this disclosure. As another non-limiting example, biological extraction database 300 may include a tissue sample table 420, which may record biological extractions obtained using tissue samples. Tables presented above are presented for exemplary purposes only; persons skilled in the art will be aware of various ways in which data may be organized in biological extraction database 300 consistently with this disclosure.

Figure 5:
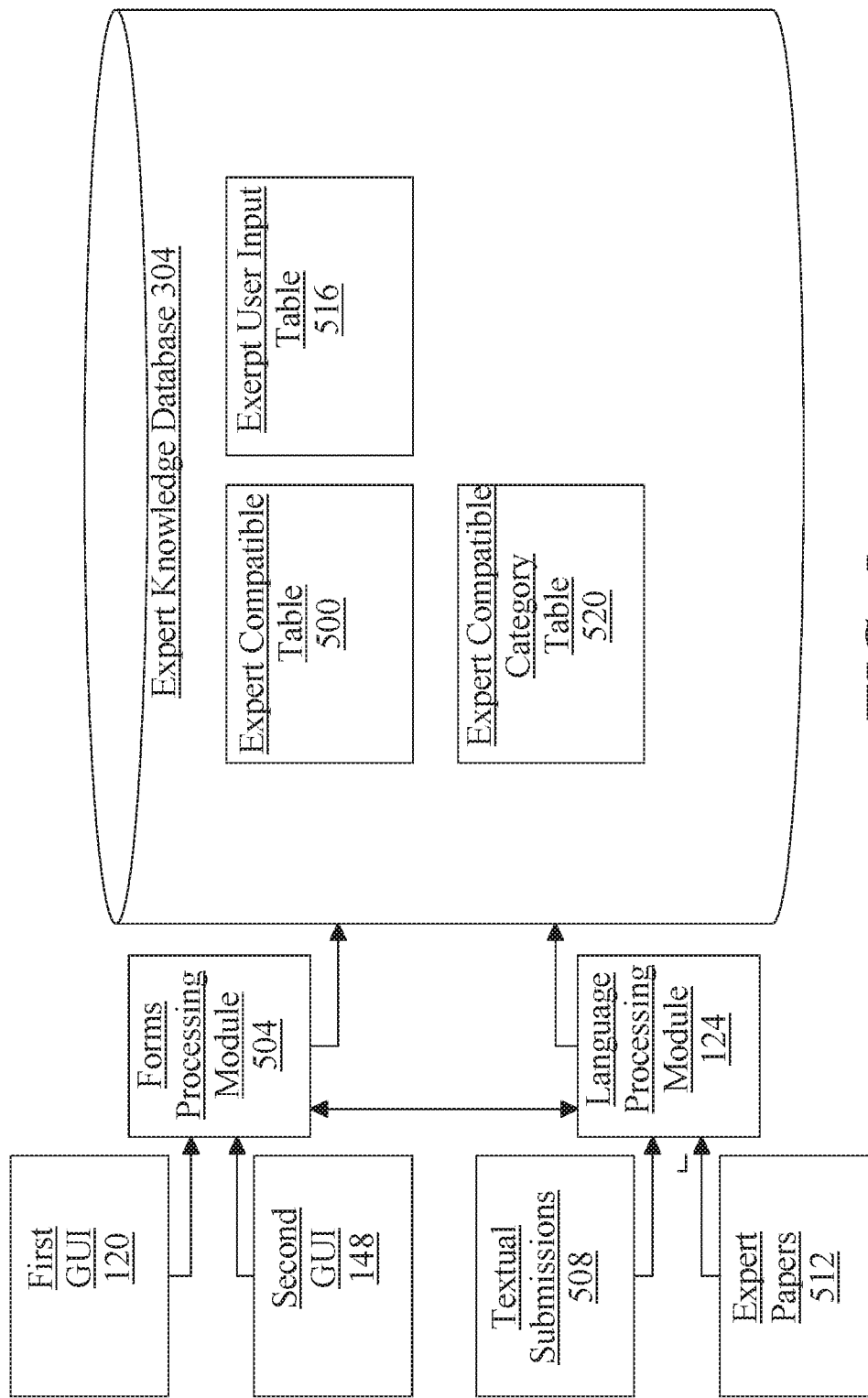
FIG. 5 is a block diagram illustrating an exemplary embodiment of an expert knowledge database.

Referring now to FIG. 5, an exemplary embodiment of an expert knowledge database 304 is illustrated. Expert knowledge database 304 may, as a non-limiting example, organize data stored in the expert knowledge database 304 according to one or more database tables. One or more database tables may be linked to one another by, for instance, common column values. For instance, a common column between two tables of expert knowledge database 304 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 5, one or more database tables in expert knowledge database 304 may include, as a non-limiting example, an expert compatible table 500. Expert compatible table 500 may be a table relating biological extraction data as described above to compatible label 116; for instance, where an expert has entered data relating a compatible label 116 to a category of biological extraction data and/or to an element of biological extraction data via first graphical user interface 120 as described above, one or more rows recording such an entry may be inserted in expert compatible table 500. In an embodiment, a forms processing module 504 may sort data entered in a submission via first graphical user interface 120 by, for instance, sorting data from entries in the first graphical user interface 120 to related categories of data; for instance, data entered in an entry relating in the first graphical user interface 120 to a compatible label 116 may be sorted into variables and/or data structures for storage of compatible label 116, while data entered in an entry relating to a category of physiological data and/or an element thereof may be sorted into variables and/or data structures for the storage of, respectively, categories of physiological data or elements of physiological data. Where data is chosen by an expert from pre-selected entries such as drop-down lists, data may be stored directly; where data is entered in textual form, language processing module 124 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module 124 may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 508, such as accomplished by filling out a paper or PDF form and/or submitting narrative information, may likewise be processed using language processing module 124. Data may be extracted from expert papers 512, which may include without limitation publications in medical and/or scientific journals, by language processing module 124 via any suitable process as described herein. Persons skilled in the art, upon reviewing the entirety of this disclosure, will be aware of various additional methods whereby novel terms may be separated from already-classified terms and/or synonyms therefore, as consistent with this disclosure. Expert compatible table 500 may include a single table and/or a plurality of tables; plurality of tables may include tables for particular categories of compatible label 116 such as books, beauty, electronics, health and personal care, home and garden, outdoors, (not shown), to name a few non-limiting examples presented for illustrative purposes only.

With continued reference to FIG. 5, one or more database tables in expert knowledge database 304 may include, an expert user input table 516, expert data populating such tables may be provided, without limitation, using any process described above, including entry of data from second graphical user interface 148 via forms processing module 504 and/or language processing module 124, processing of textual submissions 508, or processing of expert papers 512. For instance, and without limitation, an expert user input table 516 may list one or categories of user input processes, and/or links of such one or more user inputs processes to compatible label 116, as provided by experts according to any method of processing and/or entering expert data as described above. As a further example an expert compatible category table 520 may list one or more expert compatible categories based on compatible label 116 and/or biological extractions including for example a compatible category table for skin care suitable for use by users who have diabetes, a compatible category table for clothing suitable for use by users who have diabetes, and a compatible category table for sporting goods suitable for use by users who have diabetes as provided by experts according to any method of processing and/or entering expert data as described above. Tables presented above are presented for exemplary purposes only; persons skilled in the art will be aware of various ways in which data may be organized in expert knowledge database 304.

Figure 6:
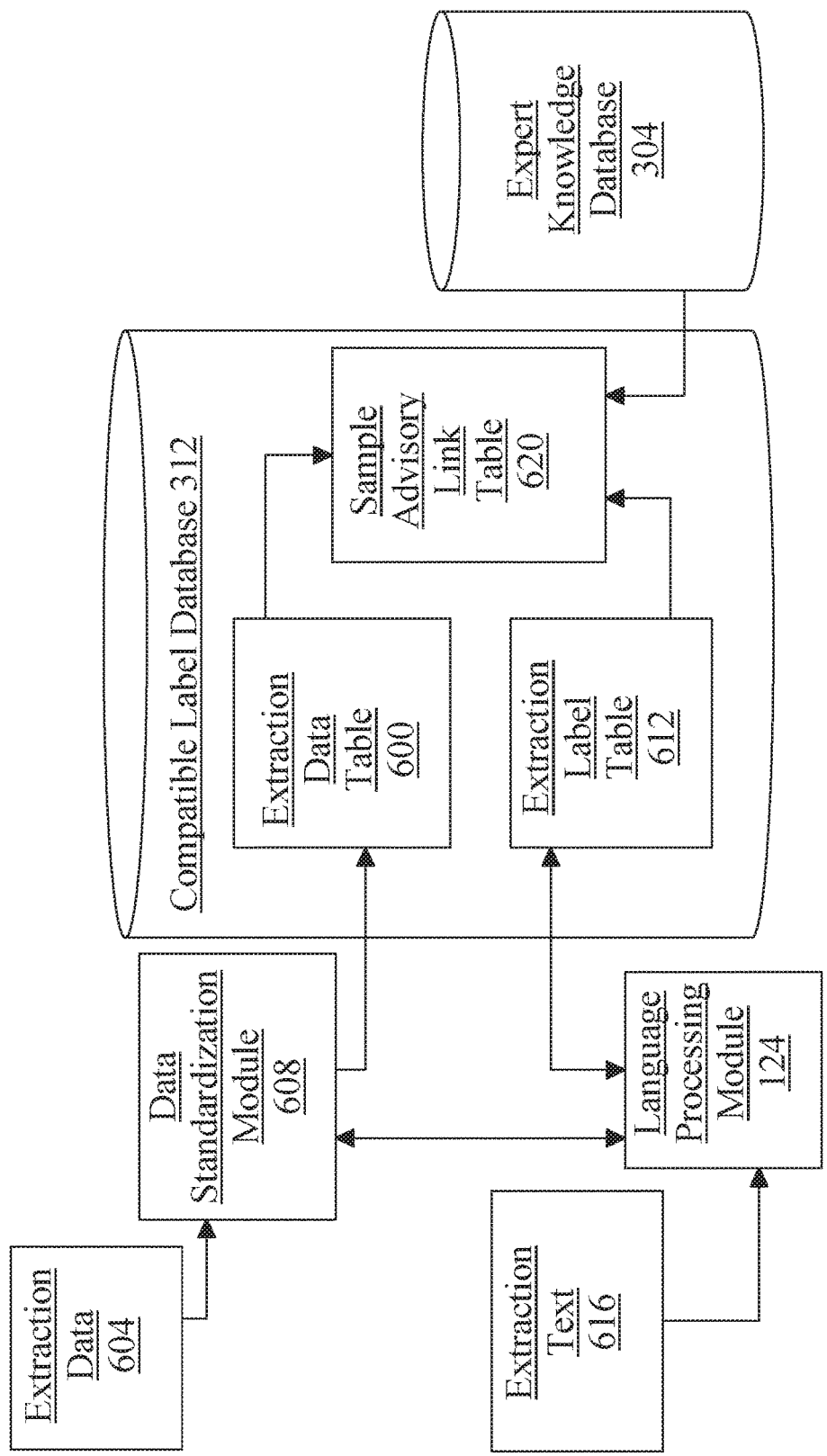
FIG. 6 is a block diagram illustrating an exemplary embodiment of a compatible label database.

Referring now to FIG. 6, an exemplary embodiment of compatible label database 312 is illustrated. Compatible label database 312 may, as a non-limiting example, organize data stored in the compatible label database 312 according to one or more database tables. One or more database tables may be linked to one another by, for instance, common column values. For instance, a common column between two tables of compatible label database 312 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 6, one or more database tables in compatible label database 312 may include, as a non-limiting example, an extraction data table 600. Extraction data table 600 may be a table listing sample data, along with, for instance, one or more linking columns to link such data to other information stored in compatible label database 312. In an embodiment, extraction data 604 may be acquired, for instance from biological extraction database 300, in a raw or unsorted form, and may be translated into standard forms, such as standard units of measurement, labels associated with particular physiological data values, or the like; this may be accomplished using a data standardization module 608, which may perform unit conversions. Data standardization module 608 may alternatively or additionally map textual information, such as labels describing values tested for or the like, using language processing module 124 or equivalent components and/or algorithms thereto.

Continuing to refer to FIG. 6, compatible label database 312 may include an extraction label table 612; extraction label table 612 may list compatible label 116 received with and/or extracted from biological extractions, for instance as received in the form of extraction text 616. A language processing module 124 may compare textual information so received to compatible label 116 and/or from new compatible label 116 according to any suitable process as described above. Extraction advisory link table 620 may combine extractions with compatible label 116, as acquired from extraction label table and/or expert knowledge database 304; combination may be performed by listing together in rows or by relating indices or common columns of two or more tables to each other. Tables presented above are presented for exemplary purposes only; persons skilled in the art will be aware of various ways in which data may be organized in expert knowledge database 304 consistently with this disclosure.

Figure 7:
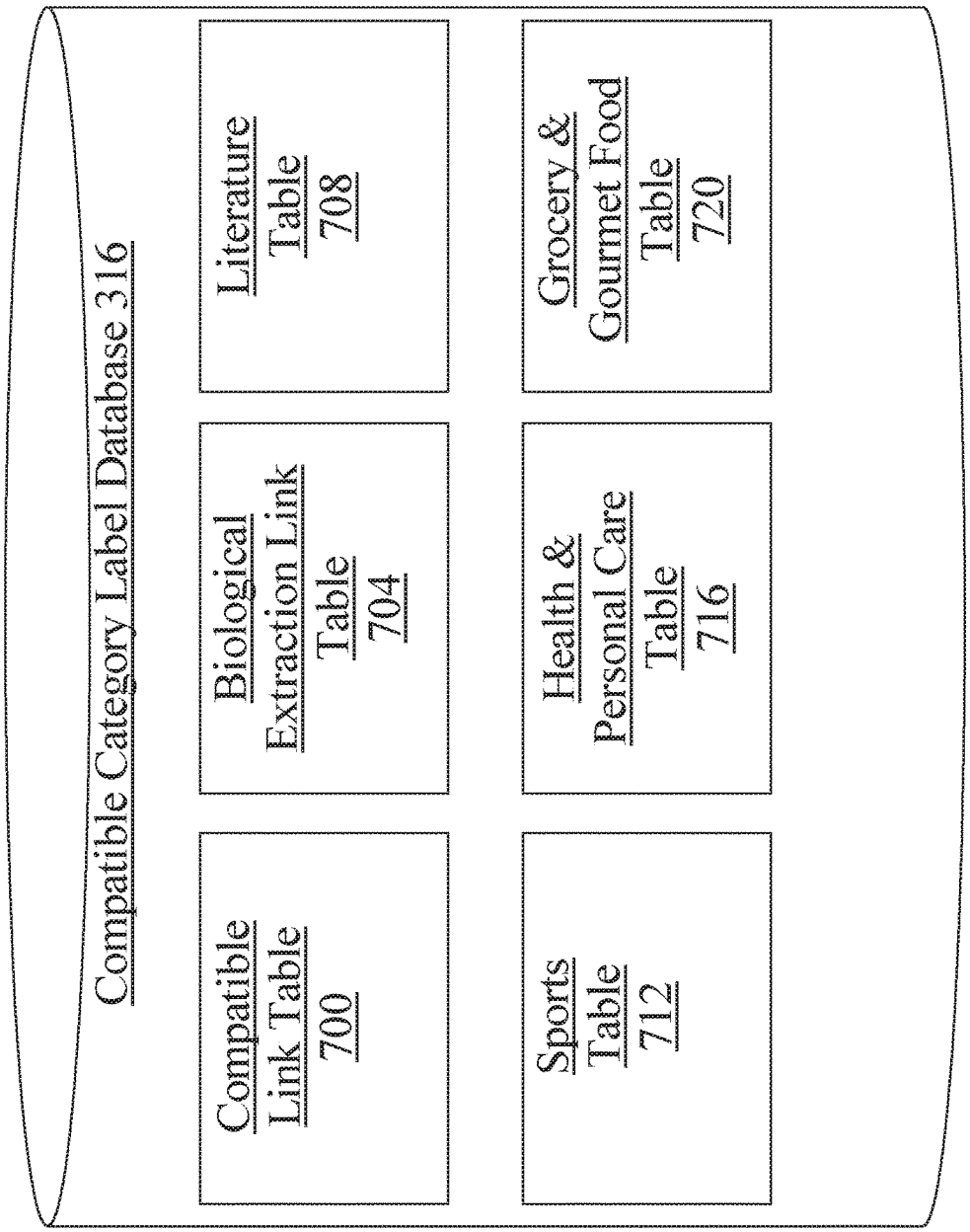
FIG. 7 is a block diagram illustrating an exemplary embodiment of a compatible category label database.

Referring now to FIG. 7, an exemplary embodiment of a compatible category label database 316 is illustrated. Compatible category label database 316 may, as a non-limiting example, organize data stored in the compatible category label database 316 according to one or more database tables. One or more database tables may be linked to one another by, for instance, common column values. For instance, a common column between two tables of compatible category label database 316 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

With continued reference to FIG. 7, compatible category label database 316 may include a compatible link table 700; compatible link table 700 may link compatible label 116 data to compatible category data, using any suitable method for linking data in two or more tables as described above. Compatible category label database 316 may include biological extraction link table 704; biological extraction link table 704 may link biological extraction data to compatible category data, using any suitable method for linking data in two or more tables as described above. Compatible category label database 316 may include literature table 708; literature table 708 may include information describing literature compatible with a given biological extraction. For example, literature table 708 may include a list of books, magazines, brochures, articles, pamphlets, and/or other reading materials that may be suitable for a user with a given biological extraction. For example, literature table 708 may include a motivational book for a user with depression or an article describing different spiritual practices for a user with cancer. Compatible category label database 316 may include sports table 712; sports table 712 may include information describing sporting equipment that may be compatible for a user with a given biological extraction. For example, sports table 712 may include information such as golf clubs, golf balls, and croquet rackets for a user with kidney disease or a user who has only one kidney and has prohibitions on playing contact sports. In yet another non-limiting example, sports table 712 may include information such as tennis rackets, tennis balls, and jogging sneakers for a user with cardiovascular disease. Compatible category label database 316 may include health and personal care table 716; health and personal care table 716 may include information describing health and personal care products that may be compatible for a user with a given biological extraction. For example, health and personal care table 716 may include information such as possible shampoos, conditioners, body wash, tooth paste and the like that do not contain synthetic estrogens or estrogen mimicking compounds for a user with CYP19A1 gene mutation. Compatible category label database 316 may include grocery and gourmet food table 720; grocery and gourmet food table 720 may include information describing grocery items and foods that may be compatible for a user with a given biological extraction. For example, grocery and gourmet food table 720 may include information such as food products such as crackers, cookies, and snacks that do not contain dairy for a user with a mutation in MCM6 gene responsible for lactase enzyme production. Compatible category label database 316 may include a single table and/or a plurality of tables; plurality of tables may include tables for particular categories of compatible label 116 such as but not limited to books, beauty, electronics, health, musical instruments, toys and games, jewelry, home and garden, outdoors, (not shown), to name a few non-limiting examples presented for illustrative purposes only.

Figure 8:
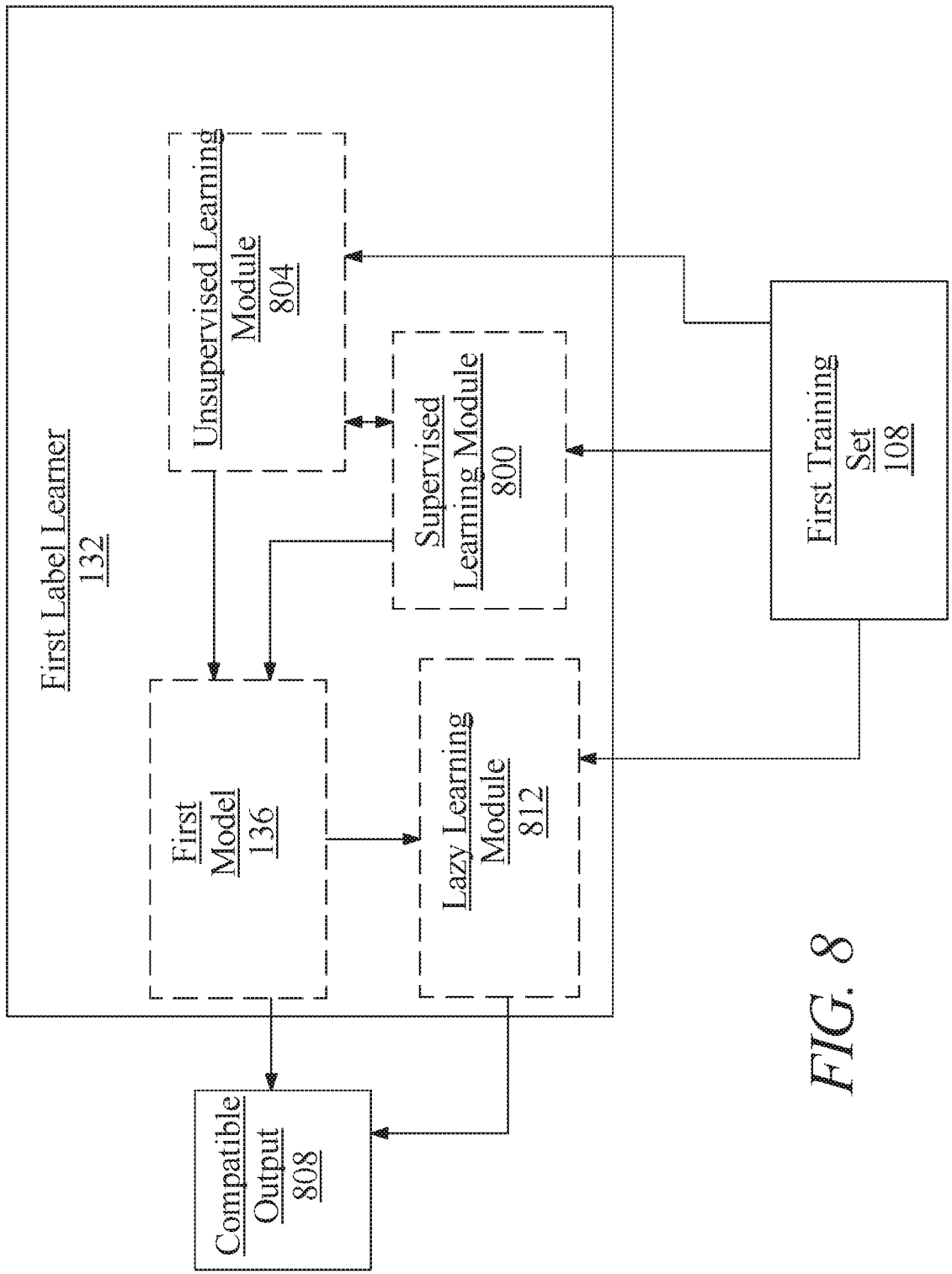
FIG. 8 is a block diagram illustrating an exemplary embodiment of a first label learner.

Referring now to FIG. 8, an exemplary embodiment of first label learner 132 is illustrated. Machine-learning algorithms used by first label learner 132 may include supervised machine-learning algorithms, which may, as a non-limiting example be executed using a supervised learning module 800 executing on at least a server 104 and/or on another computing device in communication with at least a server 104, which may include any hardware or software module. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of physiological data as inputs, compatible label 116 as outputs, and a scoring function representing a desired form of relationship to be detected between elements of physiological data and compatible label 116; scoring function may, for instance, seek to maximize the probability that a given element of physiological data and/or combination of elements of physiological is associated with a given compatible label 116 and/or combination of compatible label 116 to minimize the probability that a given element of physiological data and/or combination of elements of physiological is not associated with a given compatible label 116 and/or combination of compatible label 116. Scoring function may be expressed as a risk function representing an "expected loss" of an algorithm relating inputs to outputs, where loss is computed as an error function representing a degree to which a prediction generated by the relation is incorrect when compared to a given input-output pair provided in first training set. Persons skilled in the art, upon reviewing the entirety of this disclosure, will be aware of various possible variations of supervised machine learning algorithms that may be used to determine relation between elements of physiological and compatible label 116. In an embodiment, one or more supervised machine-learning algorithms may be restricted to a particular domain for instance, a supervised machine-learning process may be performed with respect to a given set of parameters and/or categories of parameters that have been suspected to be related to a given set of compatible label 116, and/or are specified as linked to a medical specialty and/or field of medicine covering a particular set of compatible label 116. As a non-limiting example, a particular set of blood test biomarkers and/or sensor data may be typically used by cardiologists to diagnose or predict various cardiovascular conditions, and a supervised machine-learning process may be performed to relate those blood test biomarkers and/or sensor data to the various cardiovascular conditions and correlated compatible products; in an embodiment, domain restrictions of supervised machine-learning procedures may improve accuracy of resulting models by ignoring artifacts in training data. Domain restrictions may be suggested by experts and/or deduced from known purposes for particular evaluations and/or known tests used to evaluate compatible label 116. Additional supervised learning processes may be performed without domain restrictions to detect, for instance, previously unknown and/or unsuspected relationships between physiological data and compatible label 116.

With continued reference to FIG. 8, machine-learning algorithms may include unsupervised processes; unsupervised processes may, as a non-limiting example, be executed by an unsupervised learning module 804 executing on at least a server 104 and/or on another computing device in communication with at least a server 104, which may include any hardware or software module. An unsupervised machine-learning process, as used herein, is a process that derives inferences in datasets without regard to labels; as a result, an unsupervised machine-learning process may be free to discover any structure, relationship, and/or correlation provided in the data. For instance, and without limitation, first label learner 132 and/or at least a server 104 may perform an unsupervised machine learning process on first training set, which may cluster data of first training set 108 according to detected relationships between elements of the first training set, including without limitation correlations of elements of physiological data to each other and correlations of compatible label 116 to each other; such relations may then be combined with supervised machine learning results to add new criteria for first label learner 132 to apply in relating diagnostic output to compatible label 116. As a non-limiting, illustrative example, an unsupervised process may determine that a first element of user physiological data acquired in a blood test correlates closely with a second element of user physiological data, where the first element has been linked via supervised learning processes to a given compatible label 116, but the second has not; for instance, the second element may not have been defined as an input for the supervised learning process, or may pertain to a domain outside of a domain limitation for the supervised learning process. Continuing the example a close correlation between first element of user physiological data and second element of user physiological data may indicate that the second element is also a good predictor for the compatible label 116; second element may be included in a new supervised process to derive a relationship or may be used as a synonym or proxy for the first physiological data element by first label learner 132.

Still referring to FIG. 8, at least a server 104 and/or first label learner 132 may detect further significant categories of user physiological data, relationships of such categories to compatible label 116, and/or categories of compatible label 116 using machine-learning processes, including without limitation unsupervised machine-learning processes as described above; such newly identified categories, as well as categories entered by experts in free-form fields as described above, may be added to pre-populated lists of categories, lists used to identify language elements for language processing module 124, and/or lists used to identify and/or score categories detected in documents, as described above. In an embodiment, as additional data is added to system 100, first label learner 132 and/or at least a server 104 may continuously or iteratively perform unsupervised machine-learning processes to detect relationships between different elements of the added and/or overall data; in an embodiment, this may enable system 100 to use detected relationships to discover new correlations between known biomarkers, and/or compatible label 116 and one or more elements of data in large bodies of data, such as genomic, proteomic, and/or microbiome-related data, enabling future supervised learning and/or lazy learning processes as described in further detail below to identify relationships between, e.g., particular clusters of genetic alleles and particular compatible label 116 and/or suitable compatible label 116. Use of unsupervised learning may greatly enhance the accuracy and detail with which system may detect compatible label 116.

With continued reference to FIG. 8, unsupervised processes may be subjected to domain limitations. For instance, and without limitation, an unsupervised process may be performed regarding a comprehensive set of data regarding one person, such as a comprehensive medical history, set of test results, and/or physiological data such as genomic, proteomic, and/or other data concerning that persons. As another non-limiting example, an unsupervised process may be performed on data concerning a particular cohort of persons; cohort may include, without limitation, a demographic group such as a group of people having a shared age range, ethnic background, nationality, sex, and/or gender. Cohort may include, without limitation, a group of people having a shared value for an element and/or category of physiological data, a group of people having a shared value for an element and/or category of compatible label 116; as illustrative examples, cohort could include all people having a certain level or range of levels of blood triglycerides, all people diagnosed with anxiety, all people with a SRD5A2 gene mutation, or the like. Persons skilled in the art, upon reviewing the entirety of this disclosure, will be aware of a multiplicity of ways in which cohorts and/or other sets of data may be defined and/or limited for a particular unsupervised learning process.

Still referring to FIG. 8, first label learner 132 may alternatively or additionally be designed and configured to generate at least a compatible output 808 by executing a lazy learning process as a function of the first training set 108 and/or at least a biological extraction; lazy learning processes may be performed by a lazy learning module 812 executing on at least a server 104 and/or on another computing device in communication with at least a server 104, which may include any hardware or software module. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at a compatible label 116 associated with a user physiological test sample, using first training set. As a non-limiting example, an initial heuristic may include a ranking of compatible label 116 according to relation to a test type of at least a physiological test sample, one or more categories of physiological data identified in test type of at least a physiological test sample, and/or one or more values detected in at least a physiological test sample; ranking may include, without limitation, ranking according to significance scores of associations between elements of physiological data and compatible label 116, for instance as calculated as described above. Heuristic may include selecting some number of highest-ranking associations and/or compatible label 116. First label learner 132 may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate compatible outputs 808 as described in this disclosure, including without limitation lazy learning applications of machine-learning algorithms as described in further detail below.

Figure 9:
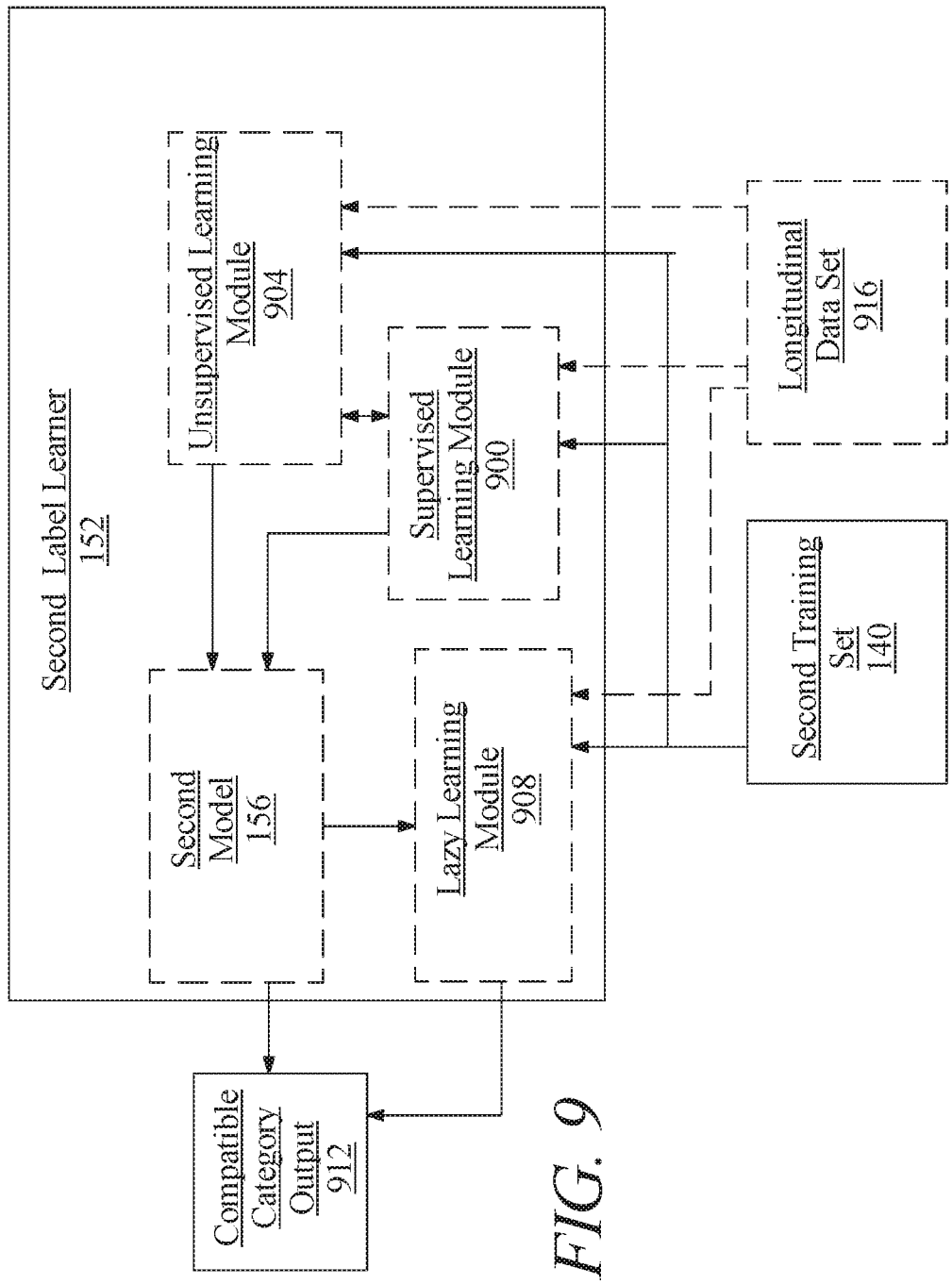
FIG. 9 is a block diagram illustrating an exemplary embodiment of a second label learner.

Referring now to FIG. 9, an exemplary embodiment of second label learner 152 is illustrated. Second label learner 152 may be configured to perform one or more supervised learning processes, as described above; supervised learning processes may be performed by a supervised learning module 900 executing on at least a server 104 and/or on another computing device in communication with at least a server 104, which may include any hardware or software module. For instance, a supervised learning algorithm may use compatible label 116 as inputs, compatible category label 144 as outputs, and a scoring function representing a desired form of relationship to be detected between compatible category label 144 and compatible label 116; scoring function may, for instance, seek to maximize the probability that a given compatible label 116 and/or combination of compatible label 116 is associated with a given compatible category label 144 to minimize the probability that a given compatible label 116 and/or combination of compatible label 116 is not associated with a given compatible category label 144 and/or combination of compatible category label 144. In an embodiment, one or more supervised machine-learning algorithms may be restricted to a particular domain; for instance, a supervised machine-learning process may be performed with respect to a given set of parameters and/or categories of compatible label 116 that have been suspected to be related to a given set of compatible category label 144, for instance because the compatible label 116 corresponding to the set of compatible category label 144 are hypothesized or suspected to have an effect on the compatible label 116, and/or are specified as linked to a particular compatible category label 144. As a non-limiting example, a particular set of compatible label 116 corresponding to a set of compatible category label 144, and a supervised machine-learning process may be performed to relate those compatible label 116 to compatible category label 144 associated with various categories including any of those categories described above such as beauty, books, electronics, entertainment, automotive and the like.

With continued reference to FIG. 9, second label learner 152 may perform one or more unsupervised machine-learning processes as described above; unsupervised processes may be performed by an unsupervised learning module 904 executing on at least a server 104 and/or on another computing device in communication with at least a server 104, which may include any hardware or software module. For instance, and without limitation, second label learner 152 and/or at least a server 104 may perform an unsupervised machine learning process on second training set 140, which may cluster data of second training set 140 according to detected relationships between elements of the second training set 140, including without limitation correlations of compatible label 116 to each other and correlations of compatible category label 144 to each other; such relations may then be combined with supervised machine learning results to add new criteria for second label learner 152 to apply in relating compatible label 116 to compatible category label 144. As a non-limiting, illustrative example, an unsupervised process may determine that a first compatible category label 144 correlates closely with a second compatible category label 144, where the first compatible category label 144 has been linked via supervised learning processes to a given compatible label 116, but the second compatible category label 144 has not; for instance, the second compatible category label 144 may not have been defined as an input for the supervised learning process, or may pertain to a domain outside of a domain limitation for the supervised learning process. Continuing the example, a close correlation between first compatible category label 144 and second compatible category label 144 may indicate that the second compatible category label 144 is also a good match for the compatible label 116; second compatible category label 144 may be included in a new supervised process to derive a relationship or may be used as a synonym or proxy for the first compatible category label 144 by second label learner 152. Unsupervised processes performed by second label learner 152 may be subjected to any domain limitations suitable for unsupervised processes performed by first label learner 132 as described above.

Continuing to view FIG. 9, second label learner 152 may be configured to perform a lazy learning process as a function of the second training set 140 and the compatible output to produce the at least a compatible category output 912; a lazy learning process may include any lazy learning process as described above regarding first label learner 132. Lazy learning processes may be performed by a lazy learning module 908 executing on at least a server 104 and/or on another computing device in communication with at least a server 104, which may include any hardware or software module. Compatible category output 912 may be provided to a user output device as described in further detail below.

In an embodiment, and still referring to FIG. 9, second label learner 152 may generate a plurality of compatible category label 144 having different implications for a particular person. For instance, where a compatible category output is related to electronics multiple compatible category label 144 may also be generated for any particular electronic device or product such as camera, cell phone, computer, tablet, phone, and the like. In such a situation, second label learner 152 and/or at least a server 104 may perform additional processes to resolve ambiguity. Processes may include presenting multiple possible results to a user, and/or providing the user with several options to pick from. Alternatively or additionally, processes may include additional machine learning steps. For instance, second label learner 152 may perform one or more lazy learning processes using a more comprehensive set of user inputs to identify a more probably correct result of the multiple results. Results may be presented and/or retained with rankings, for instance to advise a user of the relative probabilities of various compatible label 116 being correct or ideal choices for a given user; alternatively or additionally, compatible category label 144 associated with a probability of success or suitability below a given threshold and/or compatible category label 144 contradicting results of the additional process, may be eliminated. As a non-limiting example, an additional process may reveal that a user is look for a particular electronic device or product such as a smart phone or computer.

Continuing to refer to FIG. 9, second label learner 152 may be designed and configured to generate further training data and/or to generate outputs using longitudinal data 916. As used herein, longitudinal data 916 may include a temporally ordered series of data concerning the same person, or the same cohort of persons; for instance, longitudinal data 916 may describe a series of compatible label 116 that have been generated for a particular user over the past year. Longitudinal data 916 may be related to one or more compatible category label 144. Second label learner 152 may track one or more elements of user data and fit, for instance, a linear, polynomial, and/or splined function to data points; linear, polynomial, or other regression across larger sets of longitudinal data, using, for instance, any regression process as described above, may be used to determine a best-fit graph or function for the effect of a given process over time on a user data parameter. Functions may be compared to each other to rank processes; for instance, a process associated with a steeper slope in curve representing improvement in a user data element, and/or a shallower slope in a curve representing a slower decline, may be ranked higher than a process associated with a less steep slope for an improvement curve or a steeper slope for a curve marking a decline. Processes associated with a curve and/or terminal data point representing a value that does not associate with a previously detected compatible label 116 may be ranked higher than one that is not so associated. Information obtained by analysis of longitudinal data 916 may be added to second training set 140.

Figure 10:
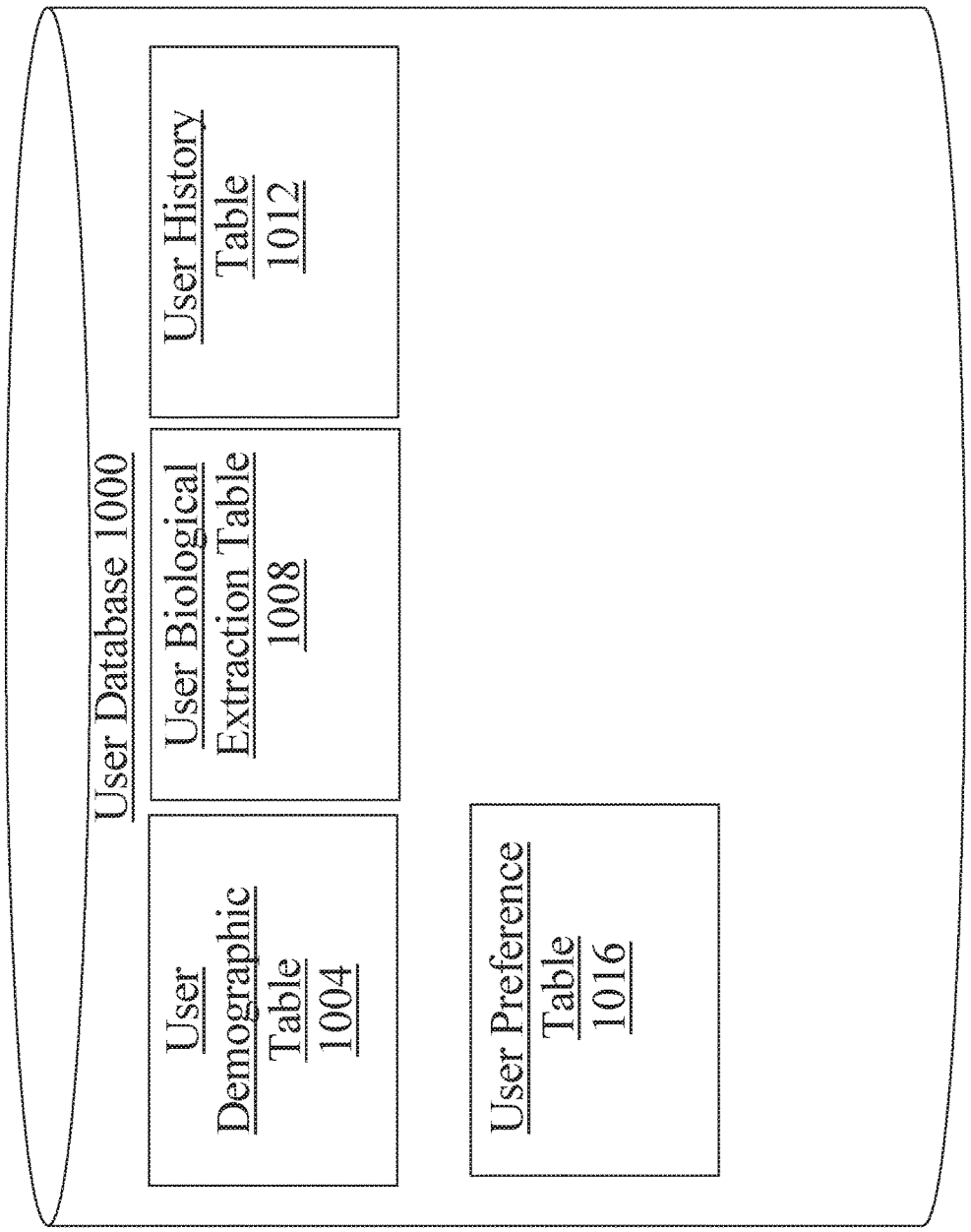
FIG. 10 is a block diagram illustrating an exemplary embodiment of a user database.

Referring now to FIG. 10, an exemplary embodiment of a user database 1000 is illustrated, which may be implemented in any manner suitable for implementation of biological extraction database 300. User database 1000 may include user information and/or preferences that may be utilized by at least a server 104 when selecting at least a first compatible element. In an embodiment, first label learner 132 and/or second label learner 152 may utilize data stored within user database 1000 to generate user specific training sets. One or more database tables in user database 1000 may include, without limitation, a user demographic table 1004; user demographic table 1004 may include information describing demographic information pertaining to user. For example, demographic table 1004 may include information describing user's name, address, phone number, race, gender, marital status, education level, employment information, total income, and the like. One or more database tables in user database 1000 may include, without limitation, a user biological extraction table 1008; user biological extraction table 1008 may include information and/or data stored about one or more biological extractions from a user. For example, user biological extraction table 1008 may include information describing results from a user's blood test and results from a saliva test. In an embodiment, user biological extraction table 1008 may be organized and/or categorized such as in chronological order, and/or by extraction type. One or more database tables in user database 1000 may include, without limitation, a user history table 1012; user history table 1012 may include information regarding history of user's interactions with system 100. For example, user history table 1012 may include data describing previous purchases a user made or previous products and/or items user browsed. In yet another non-limiting example, user history table 1012 may include information such as products and/or ingredients that a user placed into an electronic shopping cart or electronic shopping basket and possibly saved for later or later came back and purchased. One or more database tables in user database 1000 may include, without limitation, user preference table 1016; user preference table 1016 may include information describing a user's preference for particular products, ingredients, and/or brands of products or ingredients. For example, user preference table 1016 may include information describing user's preference for a particular brand of shampoo user routinely purchases or user's preference for a particular company's line of cleaning products. In an embedment, user preference table 1016 may include information regarding a user's preference for a particular product or ingredient based on a ranking or review that user may have attributed to a particular product or ingredient. Information contained within user database 1000 may be obtained from user client device 160 and/or through information provided through first graphical user interface 120 or second graphical user interface 148.

Figure 11:
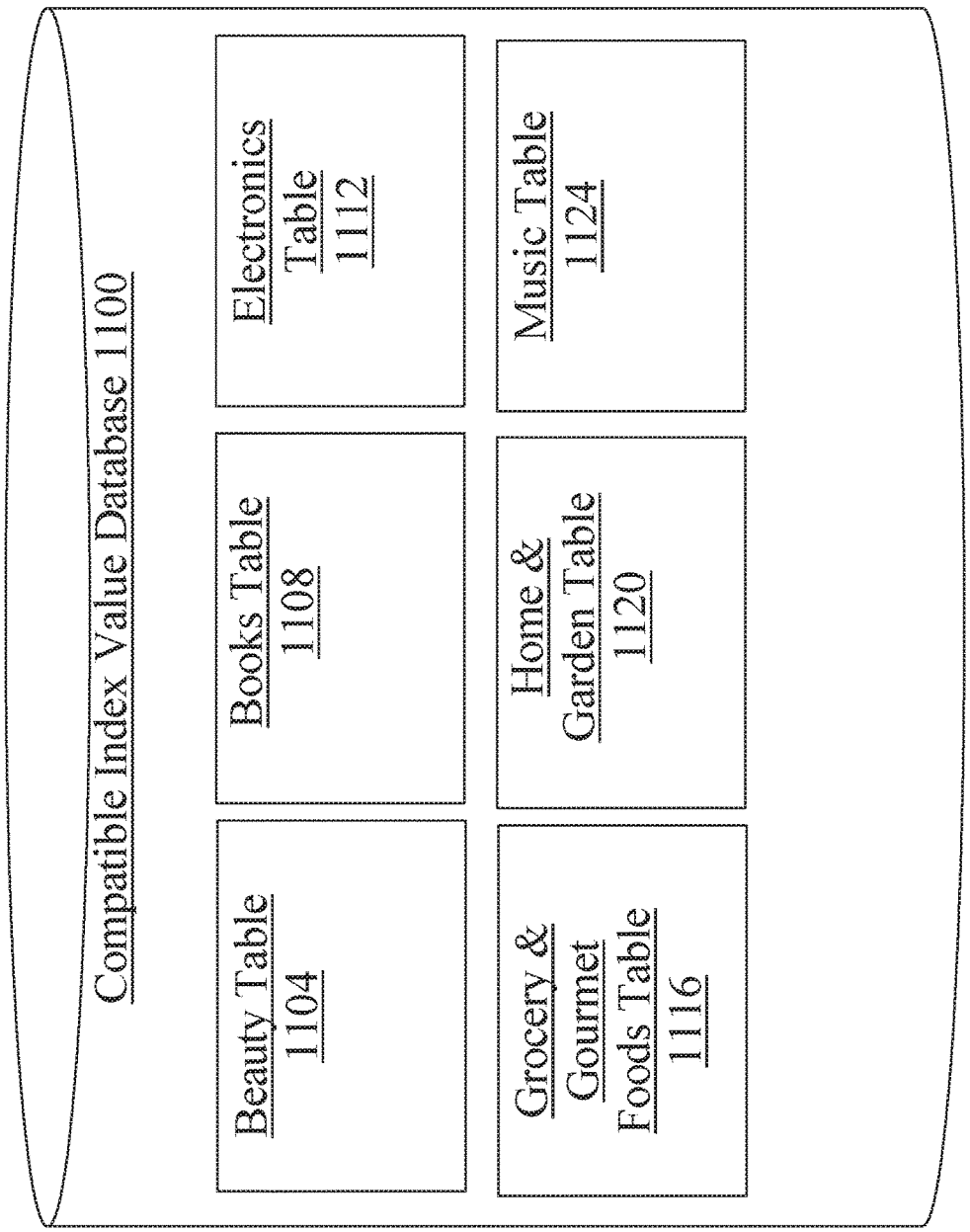
FIG. 11 is a block diagram illustrating an exemplary embodiment of a compatible index value database.

Referring now to FIG. 11, an exemplary embodiment of compatible index value database 1100 is illustrated, which may be implemented in any manner suitable for implementation of biological extraction database 300. Compatible index value database 1100 may include information describing compatible index values for different products and/or items. Compatible index value database 1100 may be consulted by at least a server 104 when selecting at least a compatible element. Compatible element index is a value assigned to a compatible element indicating a degree of similarity between a first compatible element and a second compatible element. Similarity may include a degree of likeness between a first compatible element and a second compatible element. Compatible element index may contain information allowing for at least a server 104 to select one or more compatible elements when a requested compatible element is not in stock, on a backorder, too expensive for user, and the like. Compatible index value database 1100 may be organized into categories of compatible elements whereby compatible elements can be selected and/or interchanged based on compatible element index of other compatible elements contained within a particular category. Categories of compatible elements contained within compatible index value database 1100 may include categories describing functionality and/or utility of different compatible elements. For example, and without limitation, categories of compatible elements contained within compatible index value database 1100 may include for example beauty, books, electronics, grocery & gourmet food, health & personal care, home & garden, music, sports, and the like. One or more database tables in compatible index value database 1100 may include, without limitation beauty table 1104; beauty table 1104 may include compatible index values for all compatible elements categorized as beauty. For example, beauty table 1104 may include compatible index values for compatible elements such as for example, skin serum, retinol cream, face wash, makeup brushes, shaving cream, face masks, face spray, eye cream, and the like. In an embodiment, compatible elements contained within beauty table 1104 may be further categorized into sub-categories such as tools, eye products, face products, body products, hair products, female beauty products, male beauty products, and the like. One or more database tables in compatible index value database 1100 may include, without limitation books table 1108; books table 1108 may include compatible index values for all compatible elements categorized as books. For example, books table 1108 may include compatible index values for compatible elements such as biographies & memoirs, children's books, history books, law books, medical books, mystery books, romance books, religious books, science fiction books, self-help books, sports & outdoor books, teen & young adult books, travel books and the like. In an embodiment, books table 1108 may be further categorized into sub-categories such as award winners, top sellers, new releases, bargain books, top twenty lists, celebrity picks, local authors, and the like. One or more database tables in compatible index value database 1100 may include, without limitation electronics table 1112; electronics table 1112 may include compatible index values for all compatible elements categorized as electronics. For example, electronics table 1112 may include compatible index values for compatible elements such as computers, printers, headphones, televisions, projectors, cell phones, tablets, video games, and the like. In an embodiment, electronics table 1112 may be further categorized into sub-categories such as devices, smart home devices, television, camera, computers, accessories, car electronics, portable electronics, software, video games, and the like. One or more database tables in compatible index value database 1100 may include, without limitation grocery and gourmet foods table 1116; grocery and gourmet foods table 1116 may include compatible index values for all compatible elements categorized as grocery and gourmet foods. For example, grocery and gourmet foods table 1116 may include compatible index values for compatible elements such as foods, beverages, food storage products, food replacements and the like. In an embodiment, groceries and gourmet foods table 1116 may be further categorized into sub-categories such as baby food, alcoholic beverages, beverages, breads and bakery, breakfast foods, candy, chocolate, dairy, cheese, plants, meal kits, frozen, meat, seafood, meat substitutes, pantries staples, and the like. One or more database tables in compatible index value database 1100 may include, without limitation home and garden table 1120; home and garden table 1120 may include compatible index value for compatible elements such as plants, seeds, garden equipment, outdoor equipment, and the like. In an embodiment, home and garden table 1120 may be further categorized into sub-categories such as plants, seeds, bulbs, patio furniture, patio seating, canopies, gazebos, planters, outdoor lighting, lawn mowers, outdoor power tools, garden sculptures, grills, and gardening tools. One or more database tables in compatible index value database 1100 may include, without limitation music table 1124; music table 1124 may include compatible index values for compatible elements such as specific songs, artists, albums, and the like. In an embodiment, music table 1124 may be further categorized into sub-categories such as Christian contemporary music, country, rap, jazz, rock, pop, classical, Broadway vocalists, R & B, vocal pop, and the like. Information contained within compatible index value database 1100 may be obtained from user client device 160 and/or through information provided through first graphical user interface 120 or second graphical user interface 148. Compatible index value database 1100 may include a single table and/or a plurality of tables; plurality of tables may include tables for particular categories of compatible elements such as health and personal care, outdoors, automotive, baby products, camera and photo, cell phone and accessories, entertainment, art, design, appliances, musical instruments, office products, personal computers, sports, sport collectibles, tools and home, (not shown), to name a few non-limiting examples presented for illustrative purposes only.

Figure 12:
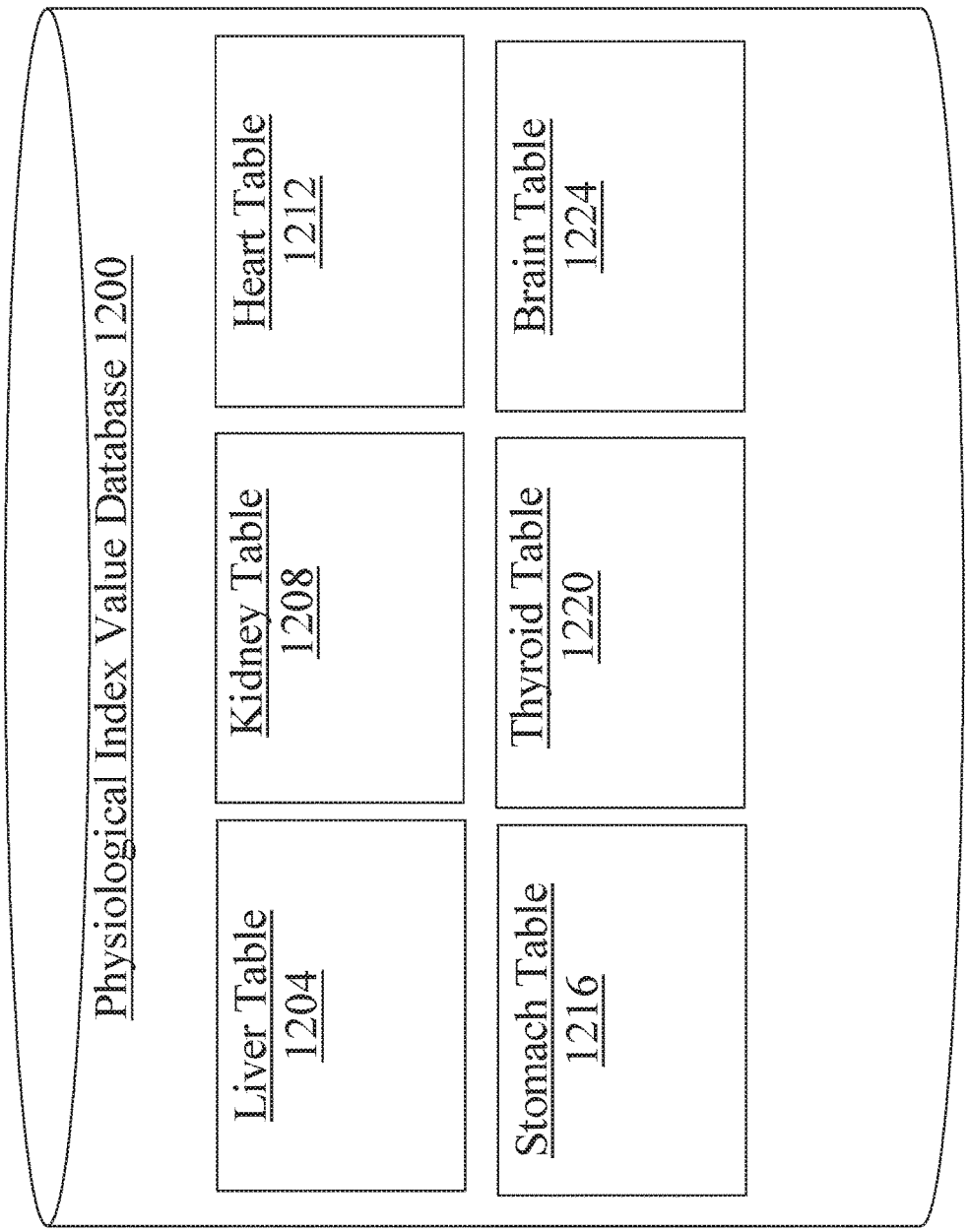
FIG. 12 is a block diagram illustrating an exemplary embodiment of a physiological index value database.

Referring now to FIG. 12, an exemplary embodiment of physiological index value database 1200 is illustrated, which may be implemented in any manner suitable for implementation of biological extraction database 300. Physiological index value database 1200 may include information describing physiological index values for different compatible elements. Physiological index value database 1200 may be consulted by at least a server 104 when selecting at least a compatible element. Physiological index value is a value assigned to a compatible element indicating a degree of similarity as to the effect on a user with a particular physiological trait, between a first compatible element and a second compatible element. Physiological index value database 1200 may include information describing ability to substitute a particular compatible element for another compatible element for a given user with a particular physiological trait. Physiological element index may contain information allowing for at least a server 104 to select one or more compatible elements and/or suggest other compatible elements for a particular user with a particular physiological trait. One or more database tables in physiological index value database 1200 may include, without limitation liver table 1204; liver table 1204 may include information describing ability to utilize and/or substitute a compatible element for a user with a particular physiological element of data relating to the liver. For example, a user with a mutation of CYP1A2 gene that affects caffeine metabolism may have snack foods selected that do not contain caffeine such as plain potato chips and pretzels while avoiding selection of snack foods that do contain caffeine such as chocolate or espresso beans. One or more database tables in physiological index value database 1200 may include, without limitation kidney table 1208; kidney table 1208 may include information describing ability to utilize and/or substitute a compatible element for a user with a particular element of physiological data relating to the kidney. For example, a user with one kidney may be able to substitute different brands of acetaminophen because acetaminophen is hepatically metabolized, but may not be able to select other pain relievers that are metabolized by the kidney such as ibuprofen. One or more database tables in physiological index value database 1200 may include, without limitation heart table 1212; heart table 1212 may include information describing ability to utilize and/or substitute a compatible element for a user with a particular physiological element of data relating to the heart. For example, a user with heart disease may be able to engage in certain sports and may purchase certain sporting equipment such as running sneakers and tennis balls but may not be able to engage in other sporting activities and at least a server 104 may not substitute running sneakers for equestrian equipment or scuba diving equipment. One or more database tables in physiological index value database 1200 may include, without limitation stomach table 1216; stomach table 1216 may include information describing ability to utilize and/or substitute a compatible element for a user with a particular element of physiological data relating to the stomach. For example, stomach table 1216 may include information describing ability to suggest different brands of multivitamins for a user with a mutation of the FUT2 gene which affects ability of user to absorb Vitamin B12 from the digestive tract at the stomach. Supplements that contain Vitamin B12 may be selected to be recommended to a user while supplements that do not contain Vitamin B12 may not be recommended to a user with a FUT2 gene. In yet another non-limiting example, a user who does not have the FUT2 gene mutation may be recommended any brand of supplement whether it contains Vitamin B12 or not. One or more database tables in physiological index value database 1200 may include, without limitation thyroid table 1220; thyroid table 1220 may include information describing ability to utilize and/or substitute a compatible element for a user with a particular element of physiological data relating to the thyroid. For example, thyroid table 1220 may include information describing ability to substitute one shampoo for another for a user with hypothyroidism who cannot tolerate synthetic estrogen disruptors found in a particular brand of shampoo. One or more database tables in physiological index value database 1200 may include, without limitation brain table 1224; brain table 1224 may include information describing ability to utilize and/or substitute a compatible element for a user with a particular element of physiological data relating to the brain. For example, brain table 1224 may include information describing ability of a user with a mutation of the DRD2 gene that produces dopamine to select certain antidepressants that boost dopamine such as duloxetine, venlafaxine, and desvenlafaxine. Physiological index value database 1200 may include a single table and/or a plurality of tables; plurality of tables may include tables for particular categories of organs such as lungs, esophagus, gallbladder, pancreases, intestines, colon, rectum, anus, bladder, lymph nodes, skin, hair, nails, spinal cord, nerves, trachea, diaphragm, bones, cartilage, ligaments, tendons (not shown), to name a few non-limiting examples presented for illustrative purposes only.

Figure 13:
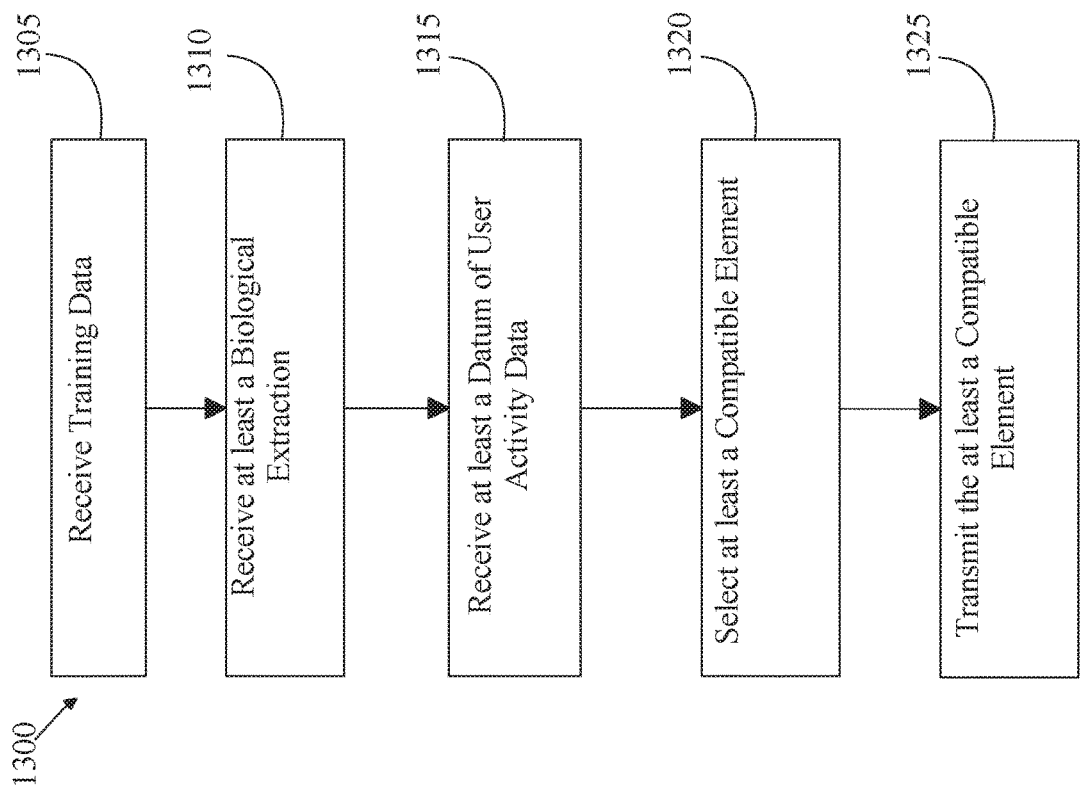
FIG. 13 is a block diagram illustrating an exemplary embodiment of a method of using artificial intelligence to select a compatible element.

Referring now to FIG. 13, an exemplary embodiment of a method 1300 of using artificial intelligence to select a compatible element is illustrated. At step 1305 at least a server 104 receives training data. Receiving training data may include receiving a first training set 108 including a plurality of first data entries, each first data entry of the plurality of first data entries including at least an element of physiological state data 112 and at least a correlated compatible label 116. Element of physiological state data 112 may include any of the physiological state data 112 as described above in reference to FIGS. 1-13. Correlated compatible label 116 may include any of the correlated compatible label 116 as described above in reference to FIGS. 1-13. In an embodiment, receiving first training set 108 may include associating the at least an element of physiological state data 112 with at least a category from a list of significant categories of physiological state data 112. In an embodiment, significant categories may be received from an expert as described above in reference to FIG. 1. Receiving training data may be performed utilizing any of the methodologies as described above in reference to FIGS. 1-13.

With continued reference to FIG. 13, at least a server 104 may be configured to receive a second training set 140. Second training set 140 may include a plurality of second data entries, each second data entry of the plurality of second data entries including at least a compatible label 116 and at least a correlated compatible category label 144. Compatible label 116 may include any of the compatible label 116 as described above in reference to FIGS. 1-13. Correlated compatible category label 144 may include any of the correlated compatible category label 144 as described above in reference to FIGS. 1-13. Receiving second training set 140 may include associating at least a compatible label 116 with at least a category from a list of significant categories of compatible label 116. Receiving second training set 140 may include associating at least a correlated compatible category label 144 with at least a category from a list of significant categories of compatible category label 144. Receiving second training set 140 may include receiving from at least an expert at least a second data entry of the plurality of second data entries. Expert may include any of the experts as described above in reference to FIGS. 1-13.

With continued reference to FIG. 13, at step 1310 at least a server 104 receives at least a biological extraction from a user. Biological extraction may include any of the biological extractions as described above in reference to FIGS. 1-13. For instance and without limitation, receiving at least a biological extraction may include receiving a datum of information describing a particular genetic mutation or a particular diagnosed condition of a user. For example, at least a server 104 may receive at least a biological extraction describing a user's diagnosis of cardiovascular disease or high blood pressure. In an embodiment, at least a biological extraction may be stored by at least a server 104 such as in memory component. In an embodiment, at least a server 104 may record at least a biological extraction from a user. Recording at least a biological extraction may be performed using any of the methodologies as described above in reference to FIGS. 1-13.

With continued reference to FIG. 13, at least a server 104 may be configured to receive a biological extraction from a user, generate at least a diagnostic output as a function of the biological extraction and select at least a compatible element as a function of the diagnostic output. In an embodiment, diagnostic output may be generated utilizing machine-learning as described above in reference to FIG. 2. In an embodiment, diagnostic output may be utilized to select at least a compatible element using machine-learning algorithms which may include any of the second machine-learning algorithms as described above in reference to FIGS. 1-13. In an embodiment, machine-learning algorithm may generate an output such as a compatible category output as a function of a training set that includes a plurality of data entries, each data entry including at least an element of diagnostic output data and a correlated compatible label 116; this may be accomplished using any machine-learning process and/or process steps as described above in reference to FIGS. 1-13. Alternatively or additionally, generating the at least a compatible category output may include executing a supervised learning process as a function of the training set and/or longitudinal data, which may be implemented as described above in reference to FIG. 1-13. Alternatively or additionally, generating the compatible category output may include executing a lazy learning process as a function of the training set and/or longitudinal data, which may be implemented as described above in reference to FIGS. 1-13. Alternatively or additionally, generating compatible category output may include creating a machine-learning model relating compatible label 116 to diagnostic outputs using a training set relating diagnostic output data to compatible label 116 and generating the compatible label 116 output using the machine-learning model; this may be implemented, without limitation, as described above in reference to FIGS. 1-13. In an embodiment, components of first training set, second training set, third training set, and fourth training set may be utilized to generate machine-learning models to select at least a compatible element. Components of training sets may include any of the components as described above in reference to FIG. 1 and FIG. 2. For example, at least a server 104 and/or diagnostic engine 128 may receive components and relate elements between first prognostic label 208 and compatible label 116 for example. In yet another non-limiting example, at least a server 104 and/or diagnostic engine 128 may receive components and relate elements between ameliorative process label 228 and compatible category label 144.

With continued reference to FIG. 13, at step 1315 at least a server 104 receives at least a datum of user activity data. At least a datum of user activity may include any of the activity data as described above in reference to FIG. 13. For instance and without limitation, at least a datum of user activity may include information describing multiple compatible elements that a user previously browsed online. In yet another non-limiting example, at least a datum of user activity may include information describing at least a compatible element that is a user is currently browsing and may have placed into an online shopping cart and/or shopping basket. In yet another non-limiting example, at least a datum of user activity may include information describing at least a compatible element that a user purchased. In yet another non-limiting example, at least a datum of user activity may include information describing an account with multiple linked shopping carts and/or shopping baskets such as if a user has a linked personal account and business account. Linking may include some shared commonality between at least two accounts. For example, linking may include a user who controls both accounts, a payment method that is used for both accounts, a shipping address that is shared by both accounts and the like. In yet another non-limiting example, at least a datum of user activity may include information describing a linked family account such as a family that has information describing user activity of different family members or multiple shopping carts and/or shopping baskets corresponding to different user habits and/or activities.

With continued reference to FIG. 13, at step 1320 at least a server 104 selects at least a compatible element as a function of the training data, biological extraction, and user data. In an embodiment, selecting at least a compatible element may include using a first machine-learning algorithm and the first training set. First machine-learning algorithm may include any of the first machine-learning algorithms as described above in reference to FIGS. 1-13. In an embodiment, first machine-learning algorithm may generate an output such as a compatible output as a function of the first training set 108 and the at least a physiological data; this may be accomplished using any machine-learning process and/or process steps as described above in reference to FIG. 1 and FIG. 8. For instance and without limitation, generating compatible output may include executing a lazy learning process as a function of the first training set 108 and the at least a physiological data, which may be implemented as described above in reference to FIG. 1 and FIG. 8 Alternatively or additionally, generating the at least a compatible output may include creating a first machine-learning model 136 relating physiological state data 112 to compatible label 116 using the first training set 108 and generating the compatible output using the first machine-learning model 136; this may be implemented, without limitation, as described above in reference to FIG. 1 and FIG. 8.

With continued reference to FIG. 13. Selecting at least a compatible element may include using a second machine-learning algorithm and the second training set 140. Second machine-learning algorithm may include any of the second machine-learning algorithms as described above in reference to FIGS. 1-13. In an embodiment, second machine-learning algorithm may generate an output such as a compatible category output as a function of the second training set 140; this may be accomplished using any machine-learning process and/or process steps as described above in reference to FIG. 1 and FIG. 9. Alternatively or additionally, generating the at least a compatible category output may include executing a supervised learning process as a function of the second training set 140 and/or longitudinal data, which may be implemented as described above in reference to FIG. 1 and FIG. 9. Alternatively or additionally, generating the compatible category output may include executing a lazy learning process as a function of the first training set 108 and/or longitudinal data, which may be implemented as described above in reference to FIG. 1 and FIG. 9. Alternatively or additionally, generating compatible category output may include creating a second machine-learning model 156 relating compatible label 116 to compatible category label 144 using the second training set 140 and generating the compatible category output using the second machine-learning model 156; this may be implemented, without limitation, as described above in reference to FIG. 1 and FIG. 8.

With continued reference to FIG. 13, at least a compatible element may be selected as a function of at least a compatible element category. Compatible element category may include any of the compatible element categories as described above in reference to FIGS. 1-13. In an embodiment, user activity data may indicate that a user repeatedly purchased a particular product such as a gluten free shampoo. In such an instance, compatible element category of shampoo may be included in a category such as beauty and personal care. In such an instance, compatible element category of beauty and personal care may be utilized to select another product and/or ingredient contained within beauty and personal care such a conditioner or a body wash. In yet another non-limiting example, a compatible element category such as electronics may be utilized to select at least a compatible element such as a printer after a user purchased an electronic such as a computer. In an embodiment, user activity data may indicate that a user browsed a particular compatible element category which may then be utilized to select at least a compatible element from the same compatible element category.

With continued reference to FIG. 13, at least a compatible element may be selected as a function of a user preference. In an embodiment, user preference for a particular category of compatible element or a particular brand of compatible element may be stored in user database 1000 as described above in more detail in reference to FIG. 10. In such an instance, at least a compatible element may be selected based on information contained within user database 1000. For example and without limitation, user may enter information into user database 1000 such as from user client device 160, first graphical user interface 120, and/or second graphical user interface 148. In such an instance, compatible element may be selected as a function of user entered information. For example, a user may have a preference for a particular category of compatible element such as a camera user is looking to purchase, or a new perfume user may desire. In yet another non-limiting example, a user may have a preference for a particular brand of compatible element that user routinely browses or is looking to try. In such an instance, compatible element may be selected based on user preference by verifying compatible element to ensure compatible element is suitable for user based on user biological extraction such as by consulting compatible index value database 1100 as described above in reference to FIG. 11 and physiological index value database 1200 as described above in reference to FIG. 12.

With continued reference to FIG. 13, at least a server 104 may select at least a compatible element as a function of at least a compatible element. In an embodiment, at least a compatible element may be utilized to select at least a compatible element such as when a first compatible element is associated with a second compatible element or when a second compatible element may be a component of or contained within a first compatible element. For example, a first compatible element such as shampoo may be utilized to select at least a compatible element such as conditioner as a function of an association between shampoo and conditioner. In yet another non-limiting example, a first compatible element such as salt may be utilized to select at least a second compatible element such as pepper as a function of an association of salt and pepper. In yet another non-limiting example, a first compatible element such as a computer may be utilized to select a second compatible element such as a mouse as a function of a mouse being a component of and utilized in conjunction with a computer. In yet another non-limiting example, a first compatible element such as a garbage can may be utilized to select at least a second compatible element such as a garbage bag as a function of a garbage bag being utilized in conjunction with a garbage bag.

With continued reference to FIG. 13, at least a server 104 may select at least a compatible element by retrieving at least a compatible element index value from a database and selecting at least a compatible element as a function of the compatible element index value. Compatible element index value may include any of the compatible element index values as described above in reference to FIG. 1 and FIG. 12. In an embodiment, compatible element index values may be stored within compatible index value database 1100 as described above in reference to FIG. 11. In an embodiment, at least a server 104 may consult compatible index value database 1100 to extract a compatible element index value and select at least a compatible element. For example, user activity data may contain information that describes a particular brand of wipes user has purchased in the past, but which may be currently unavailable. In such an instance, at least a server 104 may retrieve at least a compatible element index value for other wipe products available. In such an instance, a product with a high compatible element index value may reflect a high degree of compatibility between the first compatible element and the second compatible element whereby the second compatible element could be selected by at least a server 104 as a function of retrieving a high compatible element index value for a particular wipe product. In yet another non-limiting example, at least a server 104 may retrieve a compatible element index value for a particular compatible element that has a very low compatible element index. In such an instance, at least a server 104 may not select the compatible element having a very low compatible element index due to a lack of compatibility between the first compatible element and the second compatible element. In an embodiment, at least a server 104 may retrieve at least a compatible element index value from compatible index value database so as to select at least a compatible element to recommend to a user to purchase and/or consider purchasing.

With continued reference to FIG. 13, at least a server 104 may select at least a compatible element by retrieving at least a compatible element physiological index value from a database and selecting at least a compatible element as a function of the compatible element physiological index value. Compatible element physiological index value may include any of the compatible element physiological index values as described above in reference to FIG. 1 and FIG. 12. In an embodiment, compatible element physiological index value may be contained in a physiological index value database such as the one described above in reference to FIG. 12. In an embodiment, at least a server 104 may consult physiological index value database to extract a physiological index value for a particular compatible element and select at least a compatible element as a function of physiological index value. For example, at least a server 104 may consult physiological index value database to select a compatible element for a user with a particular element of physiological data and/or diagnosis. For example, at least a server 104 may retrieve at least a compatible element physiological index value from physiological index value database when selecting at least a compatible element for a user with Chron's disease. In such an instance, a compatible element that contains a high physiological index value may be selected and may be substituted and/or recommended to a user with Chron's disease for example. In yet another non-limiting example, a compatible element with a low physiological index value may not be recommended for a user with anxiety or any other biological extraction and/or physiological data as described above.

With continued reference to FIG. 13, at step 1325 at least a server transmits the at least a compatible element to a user client device. Transmission may occur using any of the methodologies as described herein. User client device may include any of the user client devices as described herein.

It is to be noted that any one or more of the aspects and embodiments described herein may be conveniently implemented using one or more machines (e.g., one or more computing devices that are utilized as a user computing device for an electronic document, one or more server 104 devices, such as a document server 104, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server 104 computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 14:
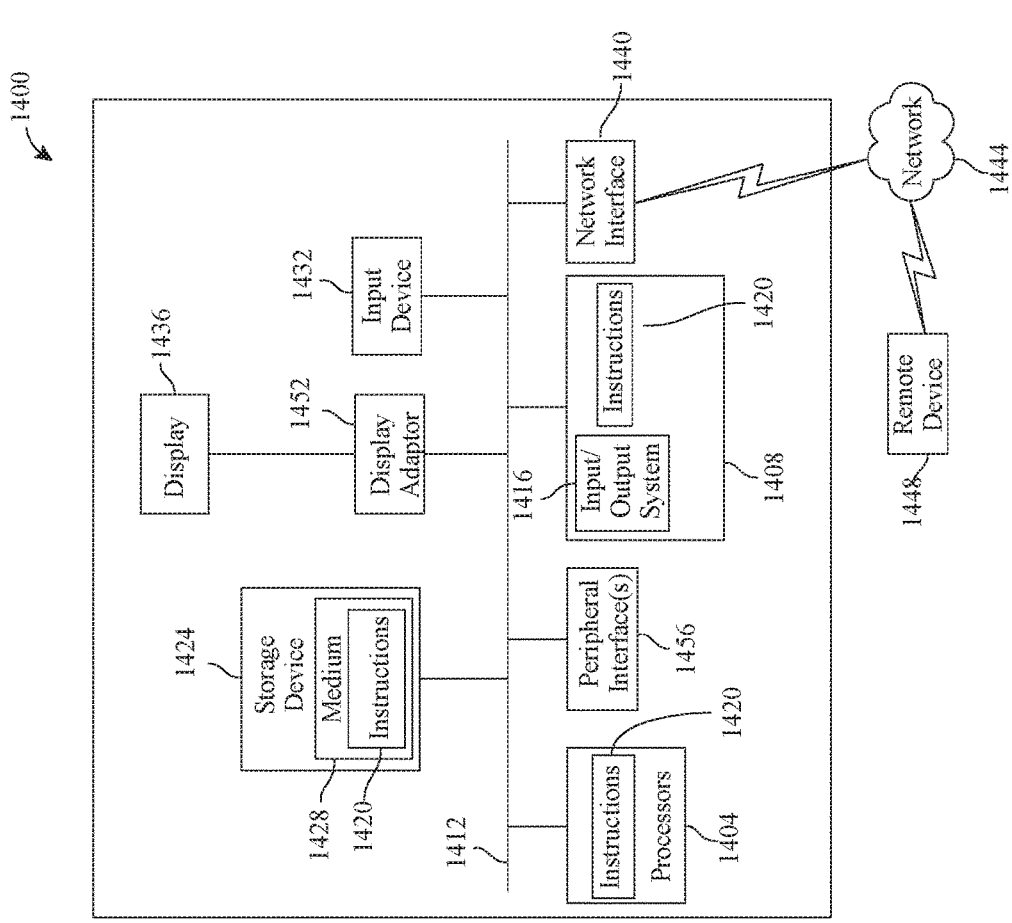
FIG. 14 is a block diagram of a computing system that can be used to implement any one or more of the methodologies disclosed herein and any one or more portions thereof.

FIG. 14 shows a diagrammatic representation of one embodiment of a computing device in the exemplary form of a computer system 1400 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1400 includes a processor 1404 and a memory 1408 that communicate with each other, and with other components, via a bus 1412. Bus 1412 may include any of several types of bus structures including, but not limited to, a memory bus, a memory controller, a peripheral bus, a local bus, and any combinations thereof, using any of a variety of bus architectures.

Memory 1408 may include various components (e.g., machine-readable media) including, but not limited to, a random access memory component, a read only component, and any combinations thereof. In one example, a basic input/output system 1416 (BIOS), including basic routines that help to transfer information between elements within computer system 1400, such as during start-up, may be stored in memory 1408. Memory 1408 may also include (e.g., stored on one or more machine-readable media) instructions (e.g., software) 1420 embodying any one or more of the aspects and/or methodologies of the present disclosure. In another example, memory 1408 may further include any number of program modules including, but not limited to, an operating system, one or more application programs, other program modules, program data, and any combinations thereof.

Computer system 1400 may also include a storage device 1424. Examples of a storage device (e.g., storage device 1424) include, but are not limited to, a hard disk drive, a magnetic disk drive, an optical disc drive in combination with an optical medium, a solid-state memory device, and any combinations thereof. Storage device 1424 may be connected to bus 1412 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1424 (or one or more components thereof) may be removably interfaced with computer system 1400 (e.g., via an external port connector (not shown)). Particularly, storage device 1424 and an associated machine-readable medium 1428 may provide nonvolatile and/or volatile storage of machine-readable instructions, data structures, program modules, and/or other data for computer system 1400. In one example, software 1420 may reside, completely or partially, within machine-readable medium 1428. In another example, software 1420 may reside, completely or partially, within processor 1404.

Computer system 1400 may also include an input device 1432. In one example, a user of computer system 1400 may enter commands and/or other information into computer system 1400 via input device 1432. Examples of an input device 1432 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1432 may be interfaced to bus 1412 via any of a variety of interfaces (not shown) including, but not limited to, a serial interface, a parallel interface, a game port, a USB interface, a FIRE-WIRE interface, a direct interface to bus 1412, and any combinations thereof. Input device 1432 may include a touch screen interface that may be a part of or separate from display 1436, discussed further below. Input device 1432 may be utilized as a user selection device for selecting one or more graphical representations in a graphical interface as described above.

A user may also input commands and/or other information to computer system 1400 via storage device 1424 (e.g., a removable disk drive, a flash drive, etc.) and/or network interface device 1440. A network interface device, such as network interface device 1440, may be utilized for connecting computer system 1400 to one or more of a variety of networks, such as network 1444, and one or more remote devices 1448 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1444, may employ a wired and/or a wireless mode of communication. In general, any network topology may be used. Information (e.g., data, software 1420, etc.) may be communicated to and/or from computer system 1400 via network interface device 1440.

Computer system 1400 may further include a video display adapter 1452 for communicating a displayable image to a display device, such as display device 1436. Examples of a display device include, but are not limited to, a liquid crystal display (LCD), a cathode ray tube (CRT), a plasma display, a light emitting diode (LED) display, and any combinations thereof. Display adapter 1452 and display device 1436 may be utilized in combination with processor 1404 to provide graphical representations of aspects of the present disclosure. In addition to a display device, computer system 1400 may include one or more other peripheral output devices including, but not limited to, an audio speaker, a printer, and any combinations thereof. Such peripheral output devices may be connected to bus 1412 via a peripheral interface 1456. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for using artificial intelligence to select a compatible element, the system comprising:
   at least a server, wherein the at least a server is designed and configured to:
      receive training data, wherein receiving training data further comprises receiving a first training set including a plurality of first data entries, each first data entry of the plurality of first data entries comprising at least an element of physiological state data and at least a correlated compatible label, wherein receiving training data further comprises using a language processing module, wherein the language processing module is configured to compare a plurality of extracted words to at least a significant category of a plurality of significant categories of the at least an element of physiological state data and the at least a correlated compatible labels, wherein the at least a significant category further comprises at least a degree of diagnostic relevance to one or more impactful conditions within at least one health field;
      receive a biological extraction from a user;
      generate, using a first machine learning model, a diagnostic output as a function of the training data and the biological extraction, wherein the diagnostic output identifies a condition of the user and a suggested exercise program, and comprises at least a prognostic label and at least an ameliorative process label;
      receive a datum of user activity data, wherein the datum of user activity comprises a list of activities and compatible elements associated with the user;
      select, using a second machine-learning model, a compatible element including an ingredient, related to the exercise program as a function of at least a compatible element category, a compatible element index value, a physiological index value, the training data, the condition of the user, and the datum of user activity data, wherein the compatible element index value is calculated based on at least a correlation between a past purchase history of the user and purchased product ingredients; and transmit the selected compatible element to a user client device.

2. The system of claim 1, wherein the at least a server is further configured to receive a second training set including a plurality of second data entries, each second data entry of the plurality of second data entries including at least a compatible label and at least a correlated compatible category label.

3. The system of claim 1, wherein the at least a server is further configured to select the compatible element further as a function of a user preference.

4. The system of claim 1, wherein the at least a server is further configured to select a second compatible element as a function of the selected compatible element.

5. The system of claim 1, wherein the at least a server is further configured to substitute the selected compatible element with a second compatible element as a function of the compatible element index value.

6. The system of claim 1, wherein selecting the compatible element further comprises retrieving a compatible element physiological index value from a database.

7. A method of using artificial intelligence to select a compatible element the method comprising:

receiving, by at least a server training data, wherein receiving training data further comprises:

receiving a first training set including a plurality of first data entries, each first data entry of the plurality of first data entries comprising at least an element of physiological state data and at least a correlated compatible label, wherein receiving training data further comprises using a language processing module, wherein the language processing module is configured to compare a plurality of extracted words to at least a significant category of a plurality of significant categories of the at least an element of physiological state data and the at least a correlated compatible labels, wherein the at least a significant category further comprises at least a degree of diagnostic relevance to one or more impactful conditions within at least one health field;

receiving, by the at least a server, a biological extraction from a user;

generating, using a first machine learning-model, a diagnostic output as a function of the training data and the biological extraction, wherein the diagnostic output identifies a condition of the user and a suggested exercise program, and comprises at least a prognostic label and at least an ameliorative process label;

receiving, by the at least a server, a datum of user activity data, wherein the datum of user activity comprises a list of activities and compatible elements associated with the user;

selecting, by the at least a server using a second machine-learning model a compatible element including an ingredient, related to the suggested exercise program as a function of at least a compatible element category, a compatible element index value, a physiological index value, the training data, the condition of the user, and the datum of user activity data, wherein the compatible element index value is calculated based on at least a correlation between a past purchase history of the user and purchased product ingredients; and transmitting, by the at least a server, the selected a compatible element to a user client device.

8. The method of claim 7, wherein receiving training data further comprises receiving a second training set including a plurality of second data entries, each second data entry of the plurality of second data entries including at least a compatible label and at least a correlated compatible category label.

9. The method of claim 7, wherein selecting the compatible element further comprises selecting the compatible element further as a function of a user preference.

10. The method of claim 7, further comprising selecting a second compatible element as a function of the selected compatible element.

11. The method of claim 7, further comprising substituting the selected compatible element with a second compatible element as a function of the compatible element index value.

12. The method of claim 7, wherein selecting the compatible element further comprises retrieving a compatible element physiological index value from a database.

* * * * *